United States Patent
Ernst et al.

(10) Patent No.: US 11,878,015 B2
(45) Date of Patent: *Jan. 23, 2024

(54) PIPERIDINE-SUBSTITUTED MNK INHIBITORS AND METHODS RELATED THERETO

(71) Applicant: eFFECTOR Therapeutics Inc., San Diego, CA (US)

(72) Inventors: Justin T Ernst, San Diego, CA (US); Paul A. Sprengeler, Escondido, CA (US); Siegfried H. Reich, La Jolla, CA (US); Samuel Sperry, Encinitas, CA (US)

(73) Assignee: eFFECTOR Therapeutics Inc., San Diego, CA (US)

( * ) Notice: Subject to any disclaimer, the term of this patent is extended or adjusted under 35 U.S.C. 154(b) by 94 days.

This patent is subject to a terminal disclaimer.

(21) Appl. No.: 17/396,187

(22) Filed: Aug. 6, 2021

(65) Prior Publication Data

US 2022/0096472 A1   Mar. 31, 2022

Related U.S. Application Data

(63) Continuation of application No. 16/233,507, filed on Dec. 27, 2018, now Pat. No. 11,083,727, which is a continuation of application No. 15/895,523, filed on Feb. 13, 2018, now abandoned.

(60) Provisional application No. 62/458,671, filed on Feb. 14, 2017.

(51) Int. Cl.
*A61K 31/506* (2006.01)
*A61P 29/00* (2006.01)
*A61P 35/00* (2006.01)
*A61P 35/02* (2006.01)

(52) U.S. Cl.
CPC ............ *A61K 31/506* (2013.01); *A61P 29/00* (2018.01); *A61P 35/02* (2018.01)

(58) Field of Classification Search
CPC ........ A61K 31/506; A61P 29/00; A61P 35/00; A61P 35/02
See application file for complete search history.

(56) References Cited

U.S. PATENT DOCUMENTS

| | | | |
|---|---|---|---|
| 5,491,144 | A | 2/1996 | Trinks et al. |
| 8,637,525 | B2 | 1/2014 | Boy et al. |
| 9,382,248 | B2 | 7/2016 | Reich et al. |
| 9,382,255 | B2 | 7/2016 | Klar et al. |
| 9,669,031 | B2 | 6/2017 | Reich et al. |
| 9,814,718 | B2 | 11/2017 | Reich et al. |
| 10,000,487 | B2 | 6/2018 | Sprengeler et al. |
| 10,112,955 | B2 | 10/2018 | Sprengeler et al. |
| 11,083,727 | B2 | 8/2021 | Justin et al. |
| 11,130,757 | B2 | 9/2021 | Reich et al. |
| 2007/0219218 | A1 | 9/2007 | Yu et al. |
| 2008/0039450 | A1 | 2/2008 | Jensen et al. |
| 2010/0105708 | A1 | 4/2010 | Jaekel et al. |
| 2011/0280886 | A1 | 11/2011 | Grzmil et al. |
| 2012/0184535 | A1 | 7/2012 | Brzozka et al. |
| 2015/0038506 | A1 | 2/2015 | Nacro et al. |
| 2015/0376181 | A1 | 12/2015 | Reich et al. |
| 2016/0303124 | A1 | 10/2016 | Webster et al. |
| 2016/0317536 | A1 | 11/2016 | Reich et al. |
| 2017/0121339 | A1 | 5/2017 | Sprengeler et al. |
| 2017/0121346 | A1 | 5/2017 | Sprengeler et al. |
| 2017/0145009 | A1 | 5/2017 | Sprengeler et al. |
| 2017/0191136 | A1 | 7/2017 | Thompson et al. |
| 2017/0266185 | A1 | 9/2017 | Reich et al. |
| 2018/0085368 | A1 | 3/2018 | Reich et al. |
| 2018/0228803 | A1 | 8/2018 | Ernst et al. |

(Continued)

FOREIGN PATENT DOCUMENTS

CL   2016003293 A1   9/2017
CN   101472912 A   7/2009

(Continued)

OTHER PUBLICATIONS

International Preliminary Report on Patentability issued in International Application No. PCT/US18/18022, dated Aug. 29, 2019, 8 pages.
International Search Report issued in International Application No. PCT/US18/18022, dated Jun. 7, 2018, 5 pages.
International Search Report and Written Opinion received for PCT Application No. PCT/US19/57656, dated Feb. 21, 2020, 10 pages.
Invitation to Pay Additional Fees received for PCT Patent International Application No. PCT/US19/57656, mailed on Dec. 26, 2019, 2 pages.

(Continued)

*Primary Examiner* — Bruck Kifle
(74) *Attorney, Agent, or Firm* — Mintz Levin Cohn Ferris Glovsky and Popeo, P.C.

(57) ABSTRACT

The present invention relates to compounds according to Formula (I):

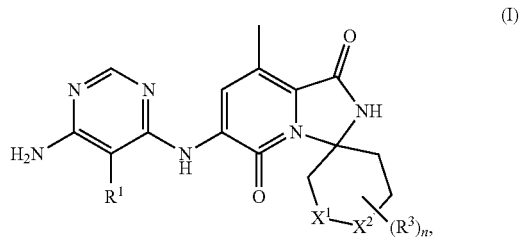

or a stereoisomer, tautomer or pharmaceutically acceptable salt thereof wherein $X^1$, $X^2$, $R^1$, $R^2$, $R^3$ and n are as defined herein. Also described are pharmaceutically acceptable compositions of Formula (I) compounds as well as methods for utilizing the compounds of Formula (I) and the pharmaceutically acceptable compositions of Formula (I) compounds as inhibitors of Mnk as well as therapeutics for the treatment of diseases such as cancer.

9 Claims, No Drawings

(56) References Cited

U.S. PATENT DOCUMENTS

| | | | |
|---|---|---|---|
| 2018/0353545 | A1 | 12/2018 | Webster et al. |
| 2019/0209560 | A1 | 7/2019 | Reich et al. |
| 2019/0275039 | A1 | 9/2019 | Ernst et al. |
| 2020/0131179 | A1 | 4/2020 | Reich et al. |
| 2021/0338673 | A1 | 11/2021 | Reich et al. |
| 2022/0119387 | A1 | 4/2022 | Reich et al. |

FOREIGN PATENT DOCUMENTS

| | | |
|---|---|---|
| CN | 101511837 A | 8/2009 |
| CN | 102186857 A | 9/2011 |
| CO | 2017000399 A2 | 4/2017 |
| ES | 2359233 T3 | 5/2011 |
| JP | 2009173629 A | 8/2009 |
| JP | 2009542749 A | 12/2009 |
| JP | 6615797 B2 | 12/2019 |
| TW | 201833102 A | 9/2018 |
| WO | 02098428 A1 | 12/2002 |
| WO | 2005000385 A1 | 1/2005 |
| WO | 2005082856 A2 | 9/2005 |
| WO | 2006020879 A1 | 2/2006 |
| WO | 2006135783 A2 | 12/2006 |
| WO | 2007021309 A1 | 2/2007 |
| WO | 2007147874 A1 | 12/2007 |
| WO | 2008006547 A2 | 1/2008 |
| WO | 2008115369 A2 | 9/2008 |
| WO | 2008117061 A2 | 10/2008 |
| WO | 2009065596 A2 | 5/2009 |
| WO | 2009112445 A1 | 9/2009 |
| WO | 2010023181 A1 | 3/2010 |
| WO | 2011014535 A1 | 2/2011 |
| WO | 2011017296 A1 | 2/2011 |
| WO | 2011106168 A1 | 9/2011 |
| WO | 2012041987 A1 | 4/2012 |
| WO | 2012075140 A1 | 6/2012 |
| WO | 2013000994 A1 | 1/2013 |
| WO | 2013043192 A1 | 3/2013 |
| WO | 2013100632 A1 | 7/2013 |
| WO | 2013147711 A1 | 10/2013 |
| WO | 2013148748 A1 | 10/2013 |
| WO | 2013151975 A1 | 10/2013 |
| WO | 2013174743 A1 | 11/2013 |
| WO | 2014044691 A1 | 3/2014 |
| WO | 2014072244 A1 | 5/2014 |
| WO | 2014088519 A1 | 6/2014 |
| WO | 2014099941 A1 | 6/2014 |
| WO | 2014128093 A1 | 8/2014 |
| WO | 2015074986 A1 | 5/2015 |
| WO | 2016096721 A1 | 6/2016 |
| WO | 2016172010 A1 | 10/2016 |
| WO | 2017085483 A1 | 5/2017 |
| WO | 2017085484 A1 | 5/2017 |
| WO | 2018152117 A1 | 8/2018 |
| WO | 2019099838 A1 | 5/2019 |
| WO | 2019103926 A1 | 5/2019 |

OTHER PUBLICATIONS

Written Opinion and International Search Report Issued in International Patent Application No. PCT/US2016/062787, dated Apr. 12, 2017, 10 pages.

International Search Report received for PCT Patent International Application No. PCT/US2015/037416, dated Sep. 17, 2015, 03 pages.

International Preliminary Report on Patentability issued in International Application No. PCT/US2015/037416, dated Jan. 5, 2017, 7 pages.

Aurora Fine Chemicals (Nov. 26, 2013) "Chemical Catalog excerpt 1481116-61-3".

Aurora Fine Chemicals (Dec. 1, 2013) "Chemical Catalog excerpt 1484631-21-1".

Aurora Fine Chemicals (Dec. 17, 2013) "Chemical Catalog excerpt 1496979-81-7".

Aurora Fine Chemicals (Dec. 29, 2013) "Chemical Catalog excerpt 1505663-52-4".

Aurora Fine Chemicals (Jan. 5, 2014) "Chemical Catalog excerpt 1511646-58-4".

Buxade, et al. (Aug. 2005) "The Mnks Are Novel Components in the Control of TNFα Biosynthesis and Phosphorylate and Regulate hnRNP A1", Immunity, 23(2):177-189.

Cao, et al. (Jun. 2018) "Inhibition of eIF4E cooperates with chemotherapy and immunotherapy in renal cell carcinoma", Clinical & Translational Oncology, 20(6):761-767.

Charrier-Savoum in, et al. (2013) "p-S6RP, p-p70S6K NS P-eif4e—Validation of three new HTRF phospho-assays or the study of translational control", Cisbio Bioassays.

Conti, et al. (2001) "MCP-1 and Rantes are Mediators of Acute and Chronic Inflammation", Allergy & Asthma Proceedings, 22(3):133-137.

Diab, et al. (Feb. 24, 2016) "Unveiling New Chemical Scaffolds as Mnk Inhibitors", Future Medicinal Chemistry, 8(3):271-285.

Effector Therapeutics, "Globenewswire 2020", Available on https:/lwww.globenewswire.cominews-4 elease/2020/05/29/2040865/0/en/eFFECTOR-sTomivosertib-Demonstrates-Positive-Phase-2-Results-for-Subjects-With-Non-Small-Cell-Lung-Cancer-in-Combination-with-Checkpoint-Inhibitors.html.

Fukunaga, et al. (Apr. 15, 1997) "MNK1, a New MAP Kinase-Activated Protein Kinase, Isolated by a Novel Expression Screening Method for Identifying Protein Kinase Substrates", The EMBO Journal, 16(8):1921-1933.

Hou, et al. (Feb. 2012) "Targeting Mnks for Cancer Therapy", 3(2):118-131.

Huang, et al. (May 30, 2020) "The MNK1/2-elF4E axis drives melanoma plasticity, progression, and resistance to immunotherapy", bioRxiv, 1-57.

Khabar, Khalid S.A (Jan. 11, 2005) "The AU-Rich Transcriptome: More Than Interferons and Cytokines, and Its Role in Disease", Journal of Interferon & Cytokine Research, 25:1-10.

Li et al. (Jul. 23, 2016) "Inhibition of Mnk Enhances Apoptotic Activity of Cytarabine in Acute Myeloid Leukemia Cells", Oncotarget, 7(35):56811-56825.

Nikolcheva, et al. (2002) "A Translational Rheostat for RFLAT-1 Regulates RANTES Expression in T Lymphocytes", The Journal of Clinical Investigation, 110(1):119-126.

Oyarzabal et al. (Sep. 23, 2010) "Discovery of Mitogen-Activated Protein Kinase-Interacting Kinase 1 Inhibitors by a Comprehensive Fragment-Oriented Virtual Screening Approach", Journal of Medicinal Chemistry, 53(18):6618-6628.

Pubmed (Feb. 23, 2016) "Tomivosertib", United State National Library of Medicine, 26 pages.

Reich, et al. (Apr. 26, 2018) "Structure-based Design of Pyridone-Aminal eFT508 Targeting Dysregulated Translation by Selective Mitogen-activated Protein Kinase Interacting Kinases 1 and 2 (MNK1/2) Inhibition", Journal of Medicinal Chemistry, 61(8):3516-3540.

Teo et al. (Sep. 2015) "An Integrated Approach for Discovery of Highly Potent and Selective Mnk Inhibitors: Screening, Synthesis and SAR Analysis", European Journal of Medicinal Chemistry, 103:539-550.

Ueda, et al. (2004) "Mnk2 and Mnk1 Are Essential for Constitutive and Inducible Phosphorylation of Eukaryotic Initiation Factor 4E but Not for Cell Growth or Development", Molecular and Cellular Biology, 24(15):6539-6549.

Venkatesh, et al. (Feb. 2000) "Role Of The Development Scientist In Compound Lead Selection And Optimization", Journal of Pharmaceutical Sciences, 89(2):145-154.

Wiedemann, et al. (2009) . . and honour their art!"—Evaluation of Historical and New Routes to 1,5-Dihydroxy-6-oxo-1,6-dihydropyridine-2-carboxylicAcid and 1,3-Dihydroxy-2-oxo-3-pyrroline-4-carboxylicAcid", A Journal of Chemical Sciences, 64b:1276-1288.

Xu, et al. (Jan. 14, 2019) "Translation control of the immune checkpoint in cancer and its therapeutic targeting", Nature Medicine, 25(2):301-311.

Charrier-Savournin et al., "p-S6RP, p-p70S6K and p-EIF4E—Validation of Three New HTRF® Phospho-assays for the Study of Translational Control" CisBio, 2013.

(56) References Cited

OTHER PUBLICATIONS

Gopal et al., "A Phase 1-2 Dose-Escalation and Cohort-Expansion Study of eFT508, a Selective, Orally Bioavailable Inhibitor of MNK1 and MNK2, in Patients with Hematological Malignancies" American Society of Hematology Annual Meeting, 2017.
Hinterneder et al., "Screening for Inhibitors of PD-1 and PD-L1 Binding with AlphaLISA Technology" PerkinElmer, Inc. (2017).

PIPERIDINE-SUBSTITUTED MNK INHIBITORS AND METHODS RELATED THERETO

CROSS-REFERENCE TO RELATED APPLICATION

This application is a continuation of U.S. patent application Ser. No. 16/233,507, filed Dec. 27, 2018, which is a continuation of U.S. patent application Ser. No. 15/895,523, filed Feb. 13, 2018, which claims the benefit of U.S. Provisional Patent Application No. 62/458,671, filed Feb. 14, 2017, the contents of which are herein incorporated by reference in their entirety.

FIELD

The present invention generally relates to compounds having activity as inhibitors of MAP kinase interacting kinase (Mnk), as well as to related compositions and methods containing or utilizing the same. Such compounds find utility in any number of therapeutic applications, including the treatment of cancer.

BACKGROUND

Eukaryotic initiation factor 4E (eIF4E) is a general translation factor, but it has the potential to enhance preferentially the translation of messenger RNAs (mRNAs) that lead to production of malignancy-associated proteins. This selectivity may relate to an increased requirement for eIF4E and its binding partners for the translation of mRNAs containing extensive secondary structure in their 5'-untranslated regions (5'-UTRs). These mRNAs include those encoding certain proteins that control cell cycle progression and tumorigenesis. Under normal cellular conditions the translation of these malignancy-associated mRNAs is suppressed as the availability of active eIF4E is limited; however, their levels can increase when eIF4E is over-expressed or hyperactivated. Elevated levels of eIF4E have been found in many types of tumors and cancer cell lines including cancers of the colon, breast, bladder, lung, prostate, gastrointestinal tract, head and neck, Hodgkin's lymphomas and neuroblastomas.

Initiation of cap-dependent translation is thought to depend on the assembly of eIF4F, an initiation factor complex including eIF4E, the scaffold protein eIF4G, and the RNA helicase eIF4A. Because eIF4E is the only one of these proteins that binds directly to the mRNA cap structure, it is the key factor for the assembly of eIF4F at the 5' cap. The scaffold protein, eIF4G, also recruits the 40S ribosomal subunit to the mRNA via its interaction with eIF3 and binds eIF4B, a protein that aids the RNA-helicase function of eIF4A, thus facilitating the translation of mRNAs that contain structured 5'-UTRs. The availability of eIF4E as part of the eIF4F complex is a limiting factor in controlling the rate of translation, and therefore eIF4E is an important regulator of mRNA translation.

Regulation of eIF4E activity forms a node of convergence of the PI3K/Akt/mTOR and Ras/Raf/MAPK signaling pathways. The PI3K (phosphoinositide 3-kinase)/PTEN (phosphatase and tensin homologue deleted on chromosome ten)/Akt/mTOR (mammalian target of rapamycin) pathway is often involved in tumorgenesis and in sensitivity and resistance to cancer therapy. Deregulated signaling through the PI3K/PTEN/Akt/mTOR pathway is often the result of genetic alterations in critical components of this pathway and/or mutations at upstream growth factor receptors or signaling components. PI3K initiates a cascade of events when activated by, for example, extracellular growth factors, mitogens, cytokines and/or receptors, PDK1 activates Akt, which in turn phosphorylates and inactivates the tumor suppressor complex comprising TSC1 and 2 (tuberous sclerosis complex 1/2), resulting in the activation of mTORC1 (target of rapamycin complex 1) by Rheb-GTP. Activation of PDK1 and Akt by PI3Ks is negatively regulated by PTEN.

PTEN is a critical tumor suppressor gene and is often mutated or silenced in human cancers. Its loss results in activation of Akt and increases downstream mTORC1 signaling. The involvement of mTOR complex1 (mTORC1) in neoplastic transformation appears to depend on its regulatory role toward the eIF4F complex; overexpression of eIF4E can confer resistance to rapamycin. mTORC1 regulates the eIF4F complex assembly that is critical for the translation of mRNAs associated with cell growth, prevention of apoptosis and transformation. mTORC1 achieves this by phosphorylation and inactivation of 4E-BPs and the subsequent dissociation of 4E-BPs from eIF4E. This then enables eIF4E to interact with the scaffold protein eIF4G, permitting assembly of the eIF4F complex for the translation of structured mRNAs. mTORC1 also promotes activation of the translational activator, S6K, which phosphorylates the ribosomal protein S6 and other substrates, including eIF4B. mTORC1 signaling is inhibited by rapamycin and its analogues (rapalogs), although these compounds act allosterically, rather than directly inhibiting mTOR kinase activity.

Given the importance of the PI3K/Akt/mTOR pathway in regulating mRNA translation of genes that encode for pro-oncogenic proteins and activated mTORC1 signaling in a high proportion of cancers, these kinases have been actively pursued as oncology drug targets. A number of pharmacological inhibitors have been identified, some of which have reached advanced clinical stages. However, it has recently become clear that the mTOR pathway participates in a complicated feedback loop that can impair activation of Akt. It has been shown that prolonged treatment of cancer cells or patients with mTOR inhibitors causes elevated PI3K activity that leads to phosphorylation of Akt and eIF4E, and promotes cancer cell survival. eIF4E, acting downstream of Akt and mTOR, recapitulates Akt's action in tumorigenesis and drug resistance, and Akt signaling via eIF4E is an important mechanism of oncogenesis and drug resistance in vivo.

In addition to the PI3K/Akt/mTOR pathway, eIF4E is also the target of the Ras/Raf/MAP signaling cascade which is activated by growth factors and for the stress-activated p38 MAP kinase pathway. Erk1/2 and p38 then phosphorylate MAP kinase-interacting kinase 1 (Mnk1) and MAP kinase-interacting kinase 2 (Mnk2). The Erk pathway is also activated in many cancers, reflecting, for example, activating mutations in Ras (found in around 20% of tumors) or loss of function of the Ras GTPase-activator protein NF 1. Mnk1 and Mnk2 are threonine/serine protein kinases and specifically phosphorylate serine 209 (Ser209) of eIF4E within the eIF4F complex, by virtue of the interaction between eIF4E and the Mnks, which serves to recruit Mnks to act on eIF4E. Mice with mutated eIF4E, in which Ser209 is replaced by alanine, show no eIF4E phosphorylation and significantly attenuated tumor growth. Significantly, while Mnk activity is necessary for eIF4E-mediated oncogenic transformation, it is dispensable for normal development. Pharmacologically inhibiting Mnks thus presents an attractive therapeutic strategy for cancer.

Despite increased understanding of Mnk structure and function, little progress has been made with regard to the discovery of pharmacological Mnk inhibitors and relatively few Mnk inhibitors have been reported: CGP052088 (Tschopp et al., *Mol Cell Biol Res Commun.* 3(4):205-211, 2000); CGP57380 (Rowlett et al., *Am J Physiol Gastrointest Liver Physiol.* 294(2):G452-459, 2008); and Cercosporamide (Konicek et al., *Cancer Res.* 71(5):1849-1857, 2011). These compounds, however, have mainly been used for the purpose of Mnk target validation. More recently, investigators have proposed further compounds for treating diseases influenced by the inhibition of kinase activity of Mnk1 and/or Mnk2, including, for example, the compounds disclosed in International Patent Application Publication WO 2014/044691 and the various patent documents cited therein, the 4-(dihydropyridinon-3-yl)amino-5-methylthieno[2,3,-d]pyrimidines disclosed by Yu et al., *European Journal of Med. Chem.*, 95: 116-126, 2015, and the 6'-(6-aminopyrimidin-4-yl)amino)-8'-methyl-2'H-spiro[cyclohexane-1,3'-imidazo[1,5-a]pyridine]-1',5'-dione and the various compounds disclosed in International Patent Application Publication WO 2015/200481.

Accordingly, while advances have been made in this field there remains a significant need in the art for compounds having improved solubility while retaining the potency to specifically inhibit Mnk and other receptor activity. The present invention fulfills this need and provides further related advantages.

SUMMARY

The present invention is directed to compounds that inhibit or modulate the activity of Mnk, as well as stereoisomers, tautomers and pharmaceutically acceptable salts of such compounds as candidate therapeutic agents. The present invention also is directed to compositions containing such compounds and associated methods for treating conditions that would benefit from Mnk inhibition, such as cancer.

In one embodiment, the invention is directed to compounds that conform to Formula (I) as well as to a stereoisomer, tautomer or pharmaceutically acceptable salt of such compounds:

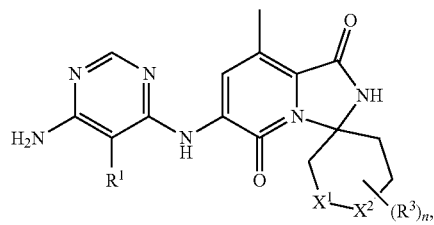

(I)

wherein:
$X^1$ is $CH_2$ and $X^2$ is $NR^2$ or $X^1$ is $NR^2$ and $X^2$ is $CH_2$;
$R^1$ is H, $(C_1\text{-}C_4)$alkyl, halogen or cyano;
$R^2$ is H, $(C_1\text{-}C_8)$alkyl or $(C_1\text{-}C_8)$haloalkyl;
$R^3$ is $(C_1\text{-}C_8)$alkyl, or $R^2$ and an adjacent $R^3$, or $R^3$ and an adjacent $R^3$, together with the ring atoms to which they are attached, form a fused five- or six-membered heterocycle or cycloalkyl ring; and
n is 0, 1, 2, 3 or 4;
wherein alkyl, heterocycle and cycloalkyl are optionally substituted with OH, CN, $NH_2$, NO2, halogen, alkyl and alkoxy.

In another embodiment, compositions are disclosed comprising a compound of structure (I) in combination with a pharmaceutically acceptable carrier, diluent or excipient.

In a further embodiment, methods are provided for treating a Mnk dependent condition in a mammal in need thereof. Such methods comprise administering an effective amount of a compound of structure (I), or compositions comprising the same, to the mammal. Such conditions include, but are not limited to, various forms of cancer as discussed in more detail below.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

In the following description, certain specific details are set forth in order to provide a thorough understanding of various embodiments of the invention. However, one skilled in the art will understand that the invention may be practiced without these details. Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

As used herein, and unless noted to the contrary, the following terms and phrases have the meaning noted below.
"Amino" refers to the —$NH_2$ substituent.
"Carboxyl" refers to the —CO2H substituent.
"Carbonyl" refers to a —C(O)— or —C(=O)— group. Both notations are used interchangeably within the specification.
"Cyano" refers to the —C≡N substituent.
"Acetyl" refers to the —C(O)$CH_3$ substituent.
"Hydroxy" or "hydroxyl" refers to the —OH substituent.
"Oxo" refers to an oxygen of —O— substituent.
The phrase "MAP kinase interacting kinase" or the term "Mnk" refers to all isoforms of the MAP kinase interacting kinase protein including Mnk-1 and Mnk-2.
"Alkyl" refers to a saturated, straight or branched hydrocarbon chain radical consisting solely of carbon and hydrogen atoms, having from one to twelve carbon atoms ($C_1$-$C_{12}$ alkyl), from one to eight carbon atoms ($C_1$-$C_8$ alkyl) or from one to six carbon atoms ($C_1$-$C_6$ alkyl), and which is attached to the rest of the molecule by a single bond. Exemplary alkyl groups include methyl, ethyl, n-propyl, 1-methylethyl (isopropyl), n-butyl, n-pentyl, 1,1-dimethylethyl (t-butyl), 3-methylhexyl, 2-methylhexyl, and the like.
"Lower alkyl" has the same meaning as alkyl defined above but having from one to four carbon atoms ($C_1$-$C_4$ alkyl).

"Alkylene" or "alkylene chain" refers to a straight or branched divalent hydrocarbon (alkyl) chain linking the rest of the molecule to a radical group, consisting solely of carbon and hydrogen, respectively. Alkylenes can have from one to twelve carbon atoms, e.g., methylene, ethylene, propylene, n-butylene, and the like. The alkylene chain is attached to the rest of the molecule through a single or double bond. The points of attachment of the alkylene chain to the rest of the molecule can be through one carbon or any two carbons within the chain. "Optionally substituted alkylene" refers to alkylene or substituted alkylene.

"Alkoxy" refers to a radical of the formula —OR$_a$ where R$_a$ is an alkyl having the indicated number of carbon atoms as defined above. Examples of alkoxy groups include without limitation —O-methyl (methoxy), —O-ethyl (ethoxy), —O-propyl (propoxy), —O— isopropyl (iso propoxy) and the like.

"Acyl" refers to a radical of the formula —C(O)R$_a$ where R$_a$ is an alkyl having the indicated number of carbon atoms.

"Aryl" refers to a hydrocarbon ring system radical comprising hydrogen, 6 to 18 carbon atoms and at least one aromatic ring. Exemplary aryls are hydrocarbon ring system radical comprising hydrogen and 6 to 9 carbon atoms and at least one aromatic ring; hydrocarbon ring system radical comprising hydrogen and 9 to 12 carbon atoms and at least one aromatic ring; hydrocarbon ring system radical comprising hydrogen and 12 to 15 carbon atoms and at least one aromatic ring; or hydrocarbon ring system radical comprising hydrogen and 15 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. "Optionally substituted aryl" refers to an aryl group or a substituted aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo (bromine), chloro (chlorine), fluoro (fluorine), or iodo (iodine).

"Haloalkyl" refers to an alkyl radical having the indicated number of carbon atoms, as defined herein, wherein one or more hydrogen atoms of the alkyl group are substituted with a halogen (halo radicals), as defined above. The halogen atoms can be the same or different. Exemplary haloalkyls are trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocyclyl", heterocycle", or "heterocyclic ring" refers to a stable 3- to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

"Heteroaryl" or "heteroarylene" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl).

The compound of the invention can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description, a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The term "effective amount" refers to an amount of a compound of the invention or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy or synergies with another therapeutic agent.

The terms "modulate", "modulation" and the like refer to the ability of a compound to increase or decrease the function, or activity of, for example, MAP kinase interacting kinase (Mnk). "Modulation", in its various forms, is intended to encompass inhibition, antagonism, partial antagonism, activation, agonism and/or partial agonism of the activity associated with Mnk. Mnk inhibitors are compounds that bind to, partially or totally block stimulation, decrease, prevent, delay activation, inactivate, desensitize, or down regulate signal transduction. The ability of a compound to modulate Mnk activity can be demonstrated in an enzymatic assay or a cell-based assay.

A "patient" or subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug that is a compound which upon administration to a patient must undergo chemical conversion by metabolic processes before becoming an active pharmacological agent. Exemplary prodrugs of compounds in accordance with Formula (I) are esters, acetamides, and amides.

Compounds of the Invention

The present invention is generally directed to compounds encompassed by the genus of Formula (I) or a stereoisomer, tautomer or pharmaceutically acceptable salt thereof.

In one embodiment $X^1$ is $CH_2$ and $X^2$ is $NR^2$. In another embodiment $X^1$ is $NR^2$ and $X^2$ is $CH_2$.

In one embodiment $R^1$ is H. In another embodiment $R^1$ is methyl. In another embodiment $R^1$ is Cl. In yet another embodiment leis cyano.

In one embodiment $R^2$ is H.

In one embodiment $R^2$ is methyl. In another embodiment $R^2$ is ethyl. In another embodiment $R^2$ is isopropyl. In another embodiment $R^2$ is tert-butyl.

In one embodiment $R^2$ is 3,3,3-trifluoropropyl. In another embodiment $R^2$ is 2,2-difluoroethyl.

In another embodiment $R^2$ is methylcyclopropane.

In one embodiment $R^3$ is H or methyl.

In one embodiment a compound according to Formula (I), or a stereoisomer, tautomer or pharmaceutically acceptable salt thereof is selected from compounds 3D, 3K, 3L, 3X, 3Y, rac-1F, 1Fa, 1Fb, rac-2F, 2Fa and 2Fb.

The inventive compounds according to Formula (I) may be isotopically-labelled by having one or more atoms replaced by an atom having a different atomic mass or mass number. Examples of isotopes that can be incorporated into compounds of according to Formula (I) include isotopes of hydrogen, carbon, nitrogen, oxygen, phosphorous, fluorine, chlorine, or iodine. Illustrative of such isotopes are $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$ and $^{125}I$, respectively. These radiolabelled compounds can be used to measure the biodistribution, tissue concentration and the kinetics of transport and excretion from biological tissues including a subject to which such a labelled compound is administered. Labeled compounds are also used to determine therapeutic effectiveness, the site or mode of action, and the binding affinity of a candidate therapeutic to a pharmacologically important target. Certain radioactive-labelled compounds according to Formula (I), therefore, are useful in drug and/or tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, affords certain therapeutic advantages resulting from the greater metabolic stability, for example, increased in vivo half-life of compounds containing deuterium. Substitution of hydrogen with deuterium may reduce dose required for therapeutic effect, and hence may be preferred in a discovery or clinical setting.

Substitution with positron emitting isotopes, such as $^{11}C$, $^{18}F$, $^{15}O$ an $^{13}N$, provides labeled analogs of the inventive compounds that are useful in Positron Emission Tomography (PET) studies, e.g., for examining substrate receptor occupancy. Isotopically-labeled compounds according to Formula (I) can generally be prepared by conventional techniques known to those skilled in the art or by processes analogous to those described in the Preparations and Examples section as set out below using an appropriate isotopic-labeling reagent.

Embodiments of the invention disclosed herein are also meant to encompass the in vivo metabolic products of compounds according to Formula (I). Such products may result from, for example, the oxidation, reduction, hydrolysis, amidation, esterification, and like processes primarily due to enzymatic activity upon administration of a compound of the invention. Accordingly, the invention includes compounds that are produced as by-products of enzymatic or non-enzymatic activity on an inventive compound following the administration of such a compound to a mammal for a period of time sufficient to yield a metabolic product. Metabolic products, particularly pharmaceutically active metabolites are typically identified by administering a radiolabelled compound of the invention in a detectable dose to a subject, such as rat, mouse, guinea pig, monkey, or human, for a sufficient period of time during which metabolism occurs, and isolating the metabolic products from urine, blood or other biological samples that are obtained from the subject receiving the radiolabelled compound.

The invention also provides pharmaceutically acceptable salt forms of Formula (I) compounds. Encompassed within the scope of the invention are both acid and base addition salts that are formed by contacting a pharmaceutically suitable acid or a pharmaceutically suitable base with a compound of the invention.

To this end, a "pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Similarly, a "pharmaceutically acceptable base addition salt" refers to those salts which retain the biological effectiveness and properties of the free acids, which are not biologically or otherwise undesirable. These salts are prepared by addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases the compounds of the invention may merely retain adventitious water or be a mixture of water plus some adventitious solvent.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

Compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

The term "tautomer" refers to a proton shift from one atom of a molecule to another atom of the same molecule. Non-limiting example of tautomers include enol/keto, lactam/lactim, amide/imidic and amine/imine forms.

Similar tautomers exist for Formula (I) compounds. The inventive compounds are synthesized using conventional synthetic methods, and more specifically using the general methods noted below. Specific synthetic protocols for several compounds in accordance with the present invention are described in the Examples.

Pharmaceutical Formulations

In one embodiment, a compound according to Formula (I) is formulated as pharmaceutically acceptable compositions that contain a Formula (I) compound in an amount effective to treat a particular disease or condition of interest upon administration of the pharmaceutical composition to a mammal. Pharmaceutical compositions in accordance with the present invention can comprise a Formula (I) compound in combination with a pharmaceutically acceptable carrier, diluent or excipient.

In this regard, a "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Further, a "mammal" includes humans and both domestic animals such as laboratory animals and household pets (e.g., cats, dogs, swine, cattle, sheep, goats, horses, rabbits), and non-domestic animals such as wildlife and the like.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by any methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

In certain embodiments a pharmaceutical composition comprising a compound of Formula I is administered to a mammal in an amount sufficient to inhibit Mnk activity upon administration, and preferably with acceptable toxicity to the same. Mnk activity of Formula (I) compounds can be determined by one skilled in the art, for example, as described in the Examples below. Appropriate concentrations and dosages can be readily determined by one skilled in the art.

Therapeutic Use

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

"Effective amount" or "therapeutically effective amount" refers to that amount of a compound of the invention which, when administered to a mammal, preferably a human, is sufficient to effect treatment, as defined below, of a Mnk related condition or disease in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

Compounds of the invention, or pharmaceutically acceptable salt thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In certain embodiments, the disclosed compounds are useful for inhibiting the activity of Mnk and/or can be useful in analyzing Mnk signaling activity in model systems and/or for preventing, treating, or ameliorating a symptom associated with a disease, disorder, or pathological condition involving Mnk, preferably one afflicting humans. A compound which inhibits the activity of Mnk will be useful in preventing, treating, ameliorating, or reducing the symptoms or progression of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mnk, such as, for example, haematological tumors, solid tumors, and/or metastases thereof, including leukaemias and myelodysplastic syndrome, malignant lymphomas, for example, B-cell lymphoma, T-cell lymphoma, hairy cell lymphoma, Hodgkin's lymphoma, non-Hodgin's lymphoma and Burkitt lymphoma, head and neck tumors including brain tumors and brain metastases, tumors of the thorax including non-small cell and small cell lung tumors, gastrointestinal tumors, endocrine tumors, mammary and other gynecological tumors, urological tumors including renal, bladder and prostate tumors, skin tumors, and sarcomas, and/or metastases thereof.

Furthermore, the inventive compounds and their pharmaceutical compositions are candidate therapeutics for the prophylaxis and/or therapy of cytokine related diseases, such as inflammatory diseases, allergies, or other conditions associated with proinflammatory cytokines. Exemplary inflammatory diseases include without limitation, chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythroderma psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from the group consisting of granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis. oesophagitis, gastritis, peritonitis, hepatitis, cholelithiasis, cholecystitis, glomerulonephritis, goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

Although inflammation is the unifying pathogenic process of these diseases, current therapies only treat the symptoms of the disease and not the underlying cause of inflammation. The compositions of the present invention are useful for the treatment and/or prophylaxis of inflammatory diseases and related complications and disorders.

Accordingly, certain embodiments are directed to a method for treating a Mnk dependent condition in a mammal in need thereof, the method comprising administering an effective amount of a pharmaceutical composition as described above (i.e., a pharmaceutical composition comprising any one or more compounds of Formula (I)) to a mammal.

"Treating" or "treatment" as used herein covers the treatment of the disease or condition of interest in a mammal, preferably a human, having the disease or condition of interest, and includes:
  (i) preventing the disease or condition from occurring in a mammal, in particular, when such mammal is predisposed to the condition but has not yet been diagnosed as having it;
  (ii) inhibiting the disease or condition, i.e., arresting its development;
  (iii) relieving the disease or condition, i.e., causing regression of the disease or condition; or
  (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

As described above deregulation of protein synthesis is a common event in human cancers. A key regulator of translational control is eIF4E whose activity is a key determinant of tumorigenicity. Because activation of eIF4E involves phosphorylation of a key serine (Ser209) specifically by MAP kinase interacting kinases (Mnk), inhibitors of Mnk are suitable candidate therapeutics for treating cell proliferative disorders such as cancer. A wide variety of cancers, including solid tumors, lymphomas and leukemias, are amenable to the compositions and methods disclosed herein. Types of cancer that may be treated include, but are not limited to adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include histiocytic disorders; leukemia; histiocytosis malignant; Hodgkin's disease; immunoproliferative small; non-Hodgkin's lymphoma; diffuse large B cell lymphoma, T-cell lymphoma, B-cell lymphoma, hairy cell lymphoma, Burkitt lymphoma, plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor.

Other cancers that can be treated using the inventive compounds include without limitation adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin.

In one embodiment the inventive compounds are candidate therapeutic agents for the treatment of cancers such as angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In a particular embodiment, the present disclosure provides methods for treating solid tumor, colon cancer, rectal cancer, colorectal cancer, bladder cancer, gastric cancer, esophageal cancer, head and neck cancer, myelodysplastic syndrome, brain cancer, CNS cancer, malignant glioma, glioblastoma, hepatocellular cancers, hepatocellular carcinoma, thyroid cancer, lung cancer, non-small cell lung cancer, a hematological cancer, leukemia, B-cell lymphoma, T-cell lymphoma, hairy cell lymphoma, diffuse large B cell lymphoma, Hodgkin's lymphoma, non-Hodgkin's lymphoma, Burkitt lymphoma, pancreatic cancer, melanoma, myeloma, multiple myeloma, pancreatic carcinoma, renal cell carcinoma, renal cancer, cervical cancer, urothelial cancer, prostate cancer, castration-resistant prostate cancer, ovarian cancer, breast cancer or triple-negative breast cancer. According to such a method, a therapeutically effective amount of at least one compound according to Formula (I) or a stereoisomer, tautomer or pharmaceutically acceptable salt thereof can be administered to a subject who has been diagnosed with a cell proliferative disease, such as a cancer. Alternatively, a pharmaceutical composition comprising at least one compound according to Formula (I) or a stereoisomer, tautomer or pharmaceutically acceptable salt thereof can be administered to a subject who has been diagnosed with cancer.

In certain embodiments, the compounds in accordance with the invention are administered to a subject with cancer in conjunction with other conventional cancer therapies such as radiation treatment or surgery. Radiation therapy is well-known in the art and includes X-ray therapies, such as gamma-irradiation, and radiopharmaceutical therapies.

In certain embodiments, the inventive Mnk inhibitor compounds are used with at least one anti-cancer agent. Anti-cancer agents include chemotherapeutic drugs. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as *vinca* alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates—busulfan, nitrosoureas (carmustine (BCNU) and analogs, streptozocin), trazenes—dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

In certain embodiments, an Mnk inhibitor in accordance with the present invention is used simultaneously, in the same formulation or in separate formulations, or sequentially with an additional agent(s) as part of a combination therapy regimen.

Mnk inhibitors according to Formula (I) including their corresponding salts and pharmaceutical compositions of Formula (I) compounds are also effective as therapeutic agents for treating or preventing cytokine mediated disorders, such as inflammation in a patient, preferably in a human. In one embodiment, a compound or composition in accordance with the invention is particularly useful for treating or preventing a disease selected from the group consisting of chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

In a further aspect of the invention, the inventive compounds or pharmaceutically acceptable formulations of the inventive compounds are provided as inhibitors of Mnk activity. Such inhibition is achieved by contacting a cell expressing Mnk with a compound or a pharmaceutically acceptable formulation, to lower or inhibit Mnk activity, to provide therapeutic efficacy for a Mnk dependent condition in a mammal in need thereof.

Therapeutically effective dosages of a compound according to Formula (I) or a composition of a Formula (I) compound will generally range from about 1 to 2000 mg/day, from about 10 to about 1000 mg/day, from about 10 to about 500 mg/day, from about 10 to about 250 mg/day, from about 10 to about 100 mg/day, or from about 10 to about 50 mg/day. The therapeutically effective dosages may be administered in one or multiple doses. It will be appreciated, however, that specific doses of the compounds of the invention for any particular patient will depend on a variety of factors such as age, sex, body weight, general health condition, diet, individual response of the patient to be treated, time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician. In any case the compound or composition will be administered at dosages and in a manner which allows a therapeutically effective amount to be delivered based upon patient's unique condition.

General Synthetic Methods

Method 1:

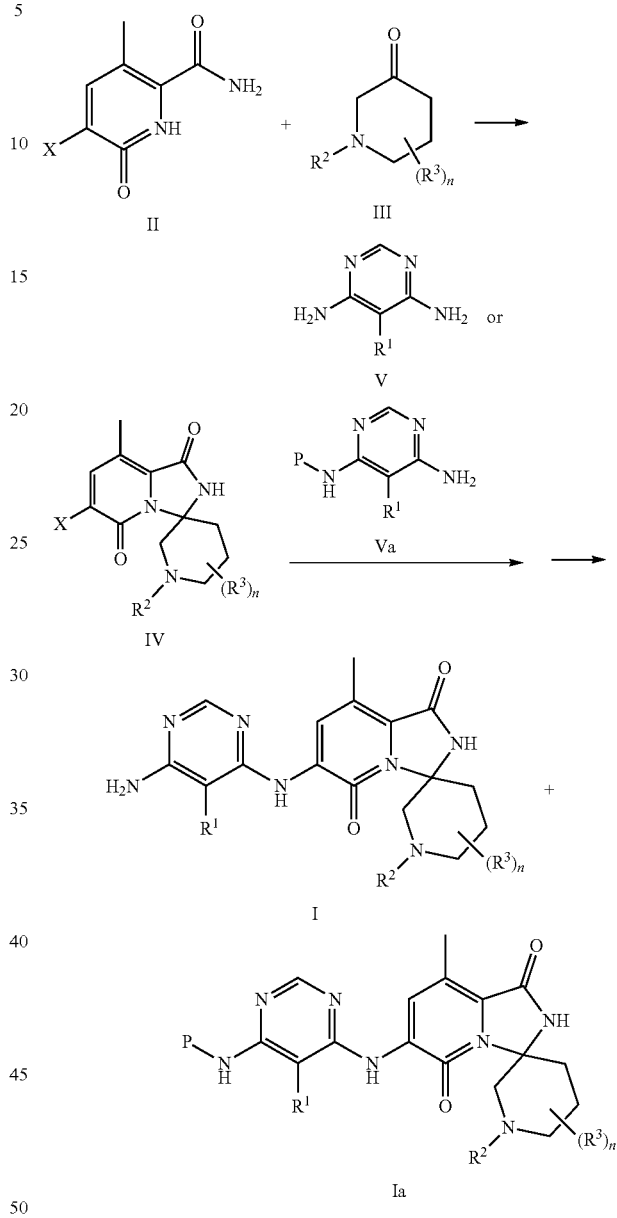

Formation of intermediate IV, where X=halogen or other leaving group, such as —OTf, —OTs or —OMs, was accomplished by exposing compound II to a ketone III, or a ketone equivalent such as IIIa, IIIb or IIIc under acidic conditions. More specifically, exposing II where X is Cl or Br to a ketone III in 1,4-dioxane and concentrated sulfuric acid with heating yields intermediate IV.

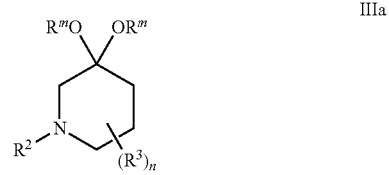

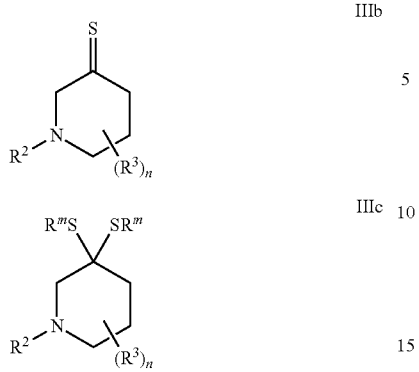

IIIb

IIIc

Formula I compounds were synthesized via Buchwald-Hartwig coupling, Ullmann-type coupling, or nucleophilic aromatic substitution. Thus, contacting intermediate IV where X=halogen or other leaving group, such as —OTf, —OTs or —OMs, with a compound of Formula V or Va under conditions suitable for coupling, or nucleophilic aromatic substitution gave Formula I or Ia compounds. Ia may be deprotected to yield I.

Method 2:

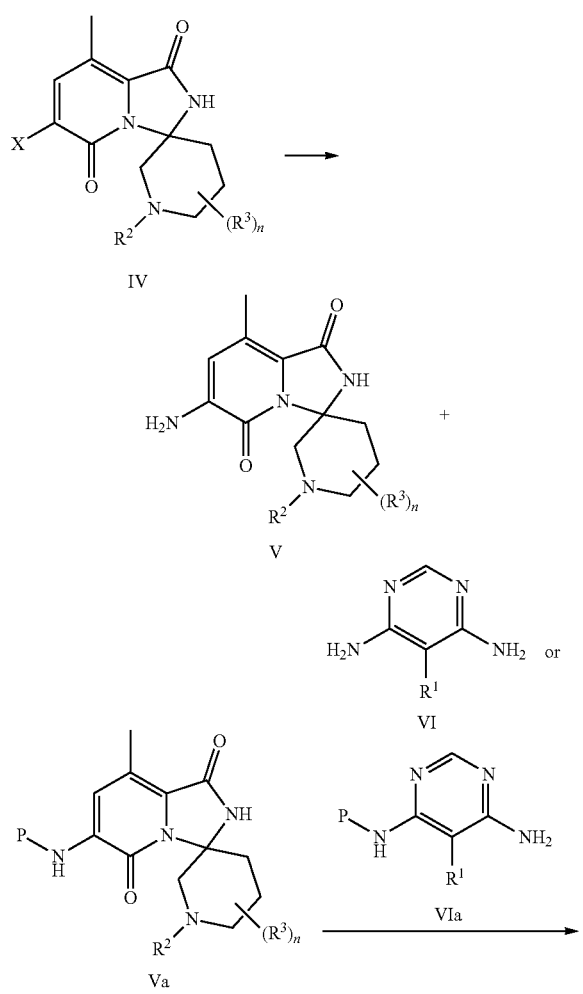

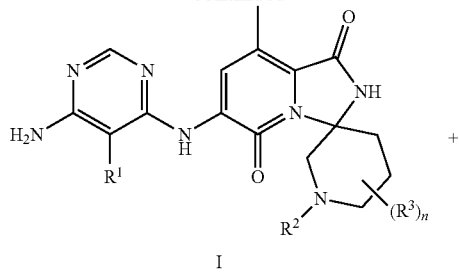

In an alternative method, the leaving group X of intermediate IV, where X=halogen or other leaving group such as —OTf, —OTs or —OMs, may be displaced with an appropriate N nucleophile under conditions similar to those described above for the synthesis of I so as to afford intermediate V or protected intermediate Va. Va may be deprotected to yield V.

Formula I or Ia compounds are readily synthesized by contacting intermediate V with a pyrimidine compound VI or VIa, 2 where X=halogen or other leaving group such as —OTf, —OTs or —OMs, under the conditions of Buchwald-Hartwig coupling, Ullmann-type coupling, or nucleophilic aromatic substitution. Ia may be deprotected to yield I.

More specific synthetic methods for Formula I compounds are set forth below. It is understood that if protecting groups ("P") are used during the synthesis of intermediates, or if a Formula I compound contains one or more protecting groups, then such protecting groups are removed by methods known in the chemical art.

It is also understood that $R^1$, $R^2$ or $R^3$ group of a Formula I compound can be furnished at a suitable stage of the synthesis via conventional methods known in the chemical art.

EXAMPLES

The following examples are provided for purpose of illustration and not limitation.

Example 1: (R)-6-(6-amino-5-methylpyrimidin-4-yl)amino)-1',8-dimethyl-2H-spiro[imidazo[1,5-a]pyridine-3,3'-piperidine]-1,5-dione (Cpd. No. 1Fa) and (S)-6-((6-amino-5-methylpyrimidin-4-yl)amino)-1',8-dimethyl-2H-spiro[imidazo[1,5-a]pyridine-3,3'-piperidine]-1,5-dione (Cpd. No. 1Fb)

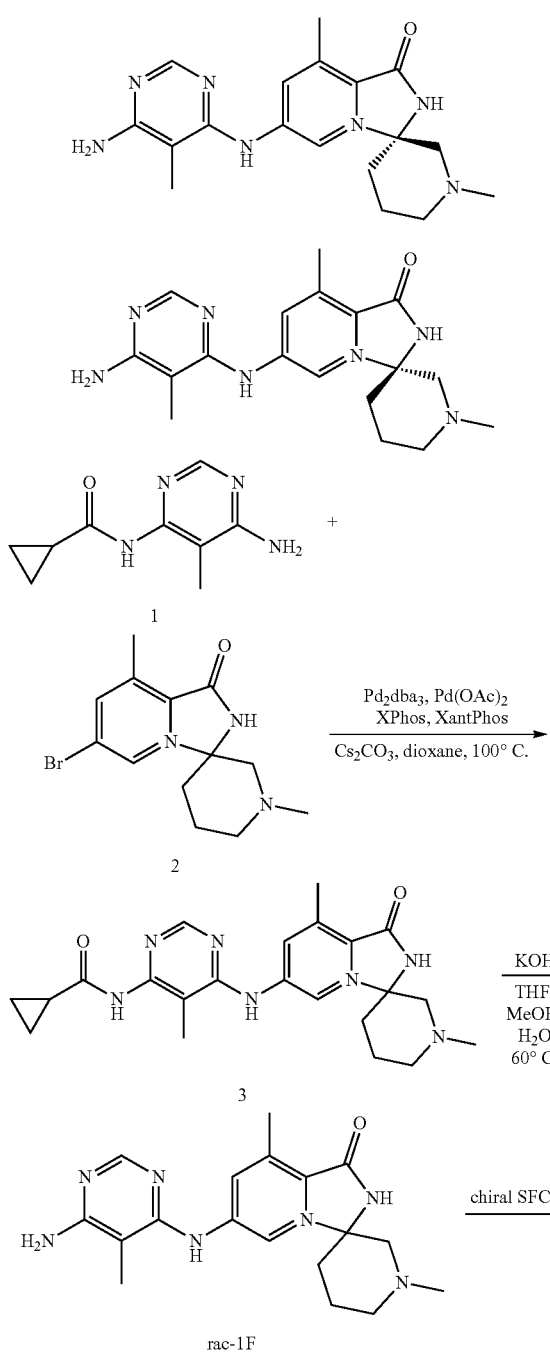

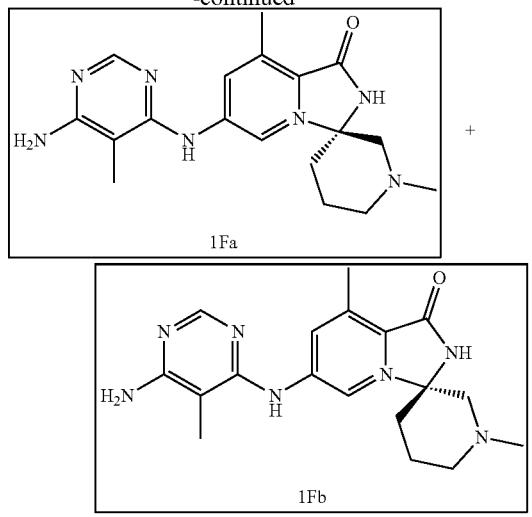

Synthesis of N-(6-(((1',8-dimethyl-1,5-dioxo-1,5-dihydro-2H-spiro[imidazo[1,5-a]pyridine-3,3'-piperidin]-6-yl)amino)-5-methylpyrimidin-4-yl)cyclopropanecarboxamide (3)

A suspension of N-(6-amino-5-methylpyrimidin-4-yl)cyclopropanecarboxamide (1, 0.82 g, 4.29 mmol), 6-bromo-1',8-dimethyl-2H-spiro[imidazo[1,5-a]pyridine-3,3'-piperidine]-1,5-dione (2, 1.40 g, 4.29 mmol), and cesium carbonate (2.79 g, 8.58 mmol) in 1,4-dioxane (20 mL) was purged with argon for 15 min. To this mixture was added 9,9-dimethyl-4,5-bis(diphenylphosphino)xanthene (0.12 g, 0.21 mmol), 2-(dicyclohexylphosphino)-2',4',6'-triisopropylbiphenyl (0.10 g, 0.21 mmol), tris(dibenzylideneacetone)dipalladium (0.20 g, 0.21 mmol) and palladium acetate (0.049 g, 0.21 mmol). The mixture was purged for another 5 min and the vial was sealed. The reaction was stirred at 100° C. for 16 h. After completion, the reaction mass was diluted with 5% methanol in dichloromethane (150 mL) and passed through a bed of celite. The filtrate was concentrated and the crude was purified by combiflash column chromatography using 3-5% methanol in dichloromethane to afford N-(6-(((1',8-dimethyl-1,5-dioxo-1,5-dihydro-2H-spiro[imidazo[1,5-a]pyridine-3,3'-piperidin]-6-yl)amino)-5-methylpyrimidin-4-yl)cyclopropanecarboxamide (3) as yellow solid. Yield: 0.96 g, 51%; MS (ESI) m/z 438.1 [M+1]⁺.

(R)-6-((6-amino-5-methylpyrimidin-4-yl)amino)-1',8-dimethyl-2H-spiro[imidazo[1,5-a]pyridine-3,3'-piperidine]-1,5-dione (Cpd. No. 1Fa) and (S)-6-((6-amino-5-methylpyrimidin-4-yl)amino)-1',8-dimethyl-2H-spiro[imidazo[1,5-a]pyridine-3,3'-piperidine]-1,5-dione (Cpd. No. 1Fb)

To a solution of N-(6-(((1',8-dimethyl-1,5-dioxo-1,5-dihydro-2H-spiro[imidazo[1,5-c]pyridine-3,3'-piperidin]-6-yl)amino)-5-methylpyrimidin-4-yl)cyclopropanecarboxamide (3, 0.95 g, 2.17 mmol) in tetrahydrofuran, ethanol and water (1:1:1, 30 mL) was added potassium hydroxide (1.22 g, 21.71 mmol). The reaction was stirred at 60° C. for 18 h. After completion, the reaction mixture was cooled to room temperature and extracted with 10% methanol in dichloromethane (3×50 mL). The combined organic layer was washed with water, brine, dried over anhydrous sodium sulfate, filtered and concentrated under reduced pressure. The crude compound was purified by combiflash column chromatography using 7-8% methanol in dichloromethane to afford 6-((6-amino-5-methylpyrimidin-4-yl)amino)-1',8-dimethyl-2H-spiro[imidazo[1,5-a]pyridine-3,3'-piperidine]-1,5-dione (rac-1F) as off white solid. Yield: 555 mg, 69%; MS (ESI) m/z 370.4 [M+1]$^+$.

The chiral purification of the racemic compound 6-((6-amino-5-methylpyrimidin-4-yl)amino)-1',8-dimethyl-2H-spiro[imidazo[1,5-a]pyridine-3,3'-piperidine]-1,5-dione (Cpd. No. 1F) was carried out by SFC chiral HPLC using a Chiralpak-IA (250×21 mm, 5 μm) column using a isocratic mixture of 15% methanol/carbon dioxide. Peak-1: R$_t$=17 min, ee=98.16%; $^1$H NMR (400 MHz, DMSO-d$_6$) δ 9.82 (bs, 1H), 8.48 (s, 1H), 8.12 (s, 1H), 7.98 (s, 1H), 6.50 (s, 2H), 3.33-3.30 (m, 1H), 3.02-2.93 (m, 1H), 2.81-2.79 (m, 1H), 2.46-2.45 (m, 1H), 2.44 (s, 3H), 2.21 (s, 3H), 1.98 (s, 3H), 1.93-1.91 (m, 2H), 1.72-1.68 (m, 1H), 1.49-1.47 (m, 1H). Peak-2: R$_t$=19.8 min, ee=96.58%; 1H NMR (400 MHz, DMSO-d$_6$) δ 9.87 (bs, 1H), 8.48 (s, 1H), 8.11 (s, 1H), 7.98 (s, 1H), 6.48 (s, 2H), 3.33-3.30 (m, 1H), 2.99-2.93 (m, 1H), 2.81-2.79 (m, 1H), 2.49-2.48 (m, 1H), 2.44 (s, 3H), 2.21 (s, 3H), 1.98 (s, 3H), 1.93-1.91 (m, 2H), 1.71-1.68 (m, 1H), 1.47 (d, J=12 Hz, 1H).

Example 2: (R)-4-amino-6-((1',8-dimethyl-1,5-dioxo-1,5-dihydro-2H-spiro[imidazo[1,5-a]pyridine-3,3'-piperidin]-6-yl)amino)pyrimidine-5-carbonitrile (Cpd. No. 2Fa) and (S)-4-amino-6-((1',8-dimethyl-1,5-dioxo-1,5-dihydro-2H-spiro[imidazo[1,5-a]pyridine-3,3'-piperidin]-6-yl)amino)pyrimidine-5-carbonitrile (Cpd. No. 2Fb)

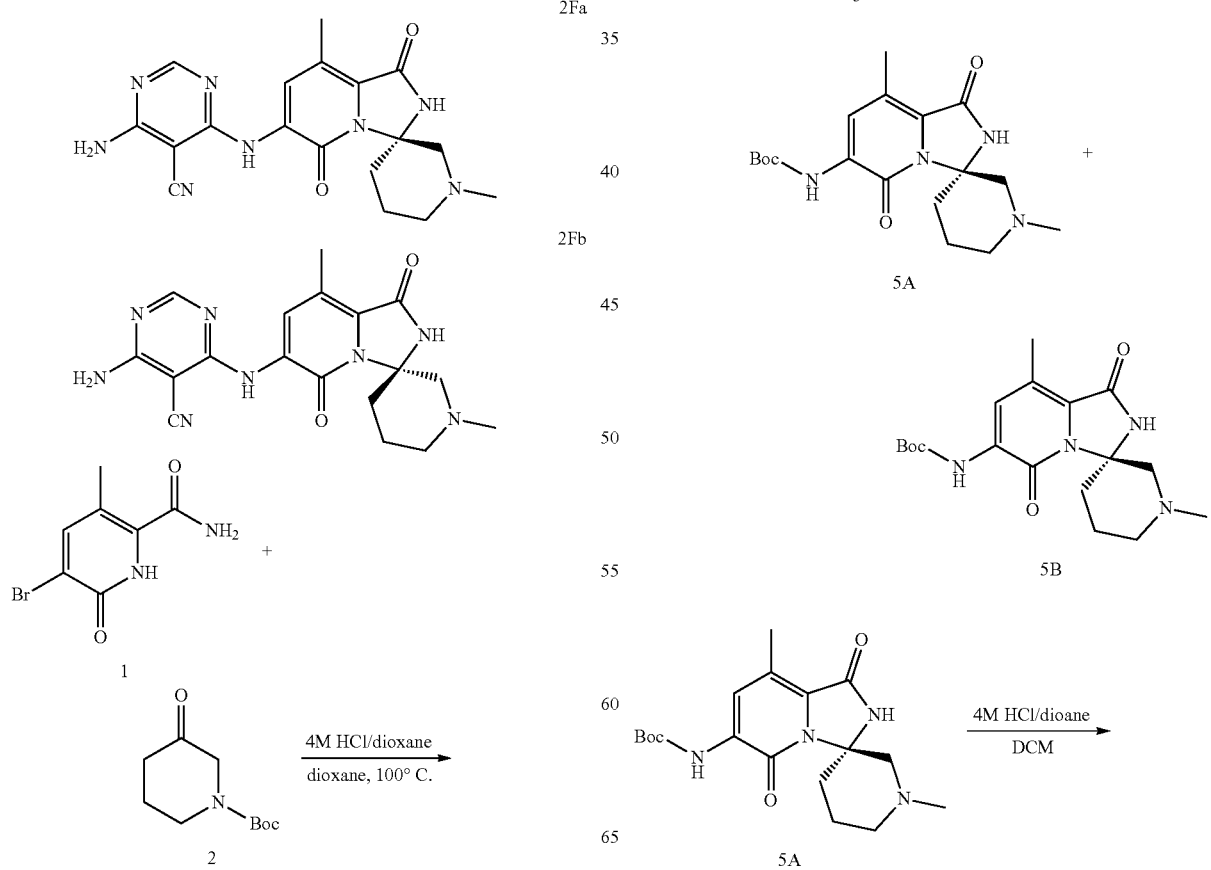

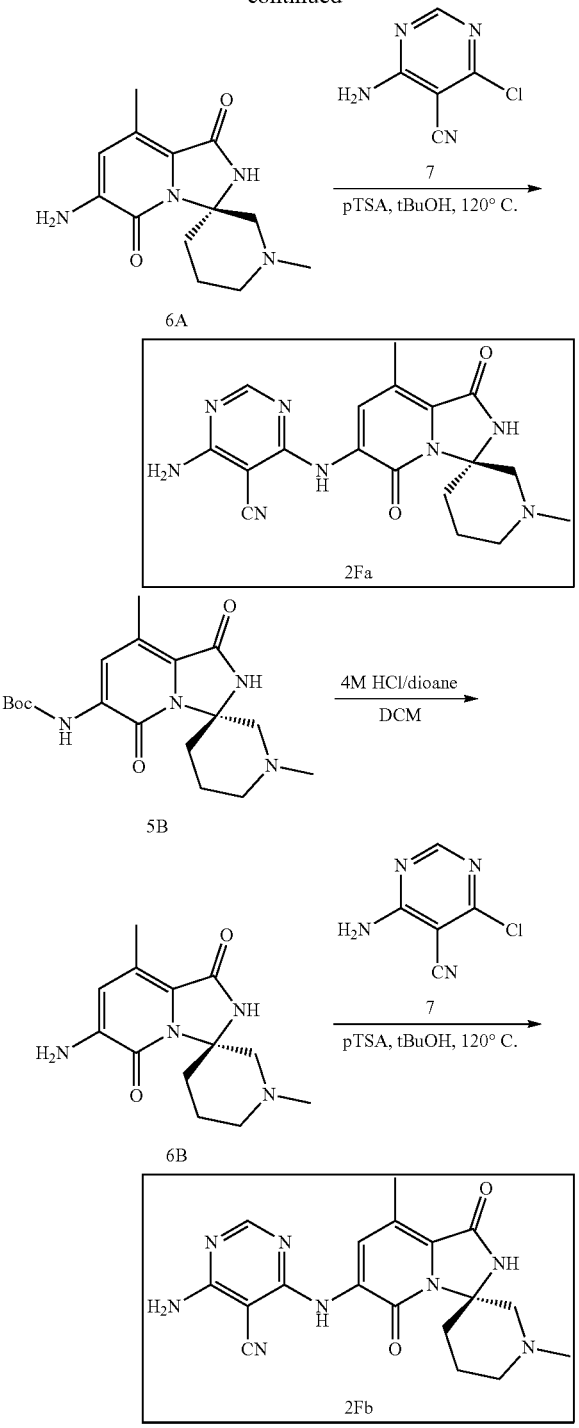

Synthesis of 6-bromo-8-methyl-2H-spiro[imidazo[1,5-a]pyridine-3,3'-piperidine]-1,5-dione Hydrochloride (3)

A sealed tube was charged with 5-bromo-3-methyl-6-oxo-1,6-dihydropyridine-2-carboxamide (1, 10.0 g, 43.2 mmol), tert-butyl 3-oxopiperidine-1-carboxylate (2, 10.31 g, 51.8 mmol) and 4 M hydrogen chloride in 1,4-dioxane (100 mL) in 1,4-dioxane (100 mL). The reaction mixture was heated at 110° C. for 16 h. After completion, the reaction mixture was evaporated under reduced pressure and the solid residue was washed with ether to afford 6-bromo-8-methyl-2H-spiro[imidazo[1,5-a]pyridine-3,3'-piperidine]-1,5-dione hydrochloride (3) as light yellow solid. Yield: 20.0 g, 93%; MS (ESI) m/z 312.27[M+1]$^+$.

Synthesis of 6-bromo-1',8-dimethyl-2H-spiro[imidazo[1,5-a]pyridine-3,3'-piperidine]-1,5-dione (4)

To a solution of 6-bromo-8-methyl-2H-spiro[imidazo[1,5-a]pyridine-3,3'-piperidine]-1,5-dione hydrochloride (3, 10.0 g, 28.8 mmol) in N,N-dimethylformamide (75 mL) were added N,N-diisopropylethylamine (9.29 g, 72.04 mmol) and methyl iodide (4.50 g, 31.7 mmol) at room temperature. The reaction mixture was stirred at room temperature for 3 h. Then the reaction mixture was quenched with ice water and the solid precipitate was isolated by filtration. The solid was washed with diethyl ether and dried under reduced pressure to afford 6-bromo-1',8-dimethyl-2H-spiro[imidazo[1,5-a]pyridine-3,3'-piperidine]-1,5-dione (4) as light brown solid. Yield: 5.3 g, 57%; MS (ESI) m/z 326.2[M+1]$^+$.

Synthesis of tert-butyl (1',8-dimethyl-1,5-dioxo-1,5-dihydro-2H-spiro[imidazo[1,5-a]pyridine-3,3'-piperidin]-6-yl)carbamate (5)

To a solution of 6-bromo-1',8-dimethyl-2H-spiro[imidazo[1,5-a]pyridine-3,3'-piperidine]-1,5-dione (4, 15.0 g, 46.1 mmol) in 1,4-dioxane (150 mL) in a sealed tube were added tert-butyl carbamate (7.01 g, 59.0 mmol) and cesium carbonate (30.0 g, 92.0 mmol) under argon atmosphere. The reaction mixture was purged with argon for 15 min followed by the addition of 9,9-dimethyl-4,5-bis(diphenylphosphino)xanthene (2.66 g, 4.6 mmol) and tris(dibenzylideneacetone)dipalladium (4.1 g, 4.60 mmol). The mixture was purged with argon for another 5 min and the reaction mixture was heated at 100° C. for 16 h. After completion, the reaction mass was concentrated under vacuum to give the crude compound which was purified by silica gel column chromatography (3-5% methanol in dichlorimethane) to afford tert-butyl (1',8-dimethyl-1,5-dioxo-1,5-dihydro-2H-spiro[imidazo[1,5-a]pyridine-3,3'-piperidin]-6-yl)carbamate (5) as a dark brown solid, which was used for the next step without any further purification. Yield: 9.0 g, 54%; MS (ESI) m/z 363.14[M+1]$^+$.

Chiral Separation of tert-butyl (R)-(1',8-dimethyl-1,5-dioxo-1,5-dihydro-2H-spiro[imidazo[1,5-a]pyridine-3,3'-piperidin]-6-yl)carbamate (5A) and Tert-butyl (S)-(1',8-dimethyl-1,5-dioxo-1,5-dihydro-2H-spiro[imidazo[1,5-a]pyridine-3,3'-piperidin]-6-yl)carbamate (5B)

The racemic compound tert-butyl (1',8-dimethyl-1,5-dioxo-1,5-dihydro-2H-spiro[imidazo[1,5-a]pyridine-3,3'-piperidin]-6-yl)carbamate (5, 8.0 g) was purified by chiral-SFC using Chiralpak-IG column (250×21 mm, 5μm) using an isocratic gradient of 0.2% triethylanime in methanol/carbon dioxide (40:60). After purification peak-1 was isolated at $R_t$=8.0 min (2.4 g, ee=99.82%) and peak-2 was isolated at $R_t$=12.8 min (3.4 g, ee=99.60%). Absolute stereochemistry of peak 1 and peak-2 were not assigned. For ease of illustration, Peak-1 was randomly assigned as tert-butyl (R)-(1',8-dimethyl-1,5-dioxo-1,5-dihydro-2H-spiro[imidazo[1,5-a]pyridine-3,3'-piperidin]-6-yl)carbamate (5A) and Peak-2 was randomly assigned as tert-butyl (S)-(1',8-dimethyl-1,5-dioxo-1,5-dihydro-2H-spiro[imidazo[1,5-a]pyridine-3,3'-piperidin]-6-yl)carbamate (5B)

Synthesis of (R)-6-amino-1',8-dimethyl-2H-spiro[imidazo[1,5-a]pyridine-3,3'-piperidine]-1,5-dione (6A)

To a solution of tert-butyl (R)-(1',8-dimethyl-1,5-dioxo-1,5-dihydro-2H-spiro[imidazo[1,5-a]pyridine-3,3'-piperidin]-6-yl)carbamate (5A, 2.40 g, 6.6 mmol) in dichloromethane (20 mL) was added 4 M hydrogen chloride in 1,4-dioxane (20 mL). The reaction mixture was stirred at room temperature for 3 h. After completion, the reaction mass was concentrated under vacuum and the crude compound was suspended in saturated solution of sodium bicarbonate. The aqueous layer was extracted with dichloromethane; the organic layer was dried over sodium sulphate, filtered and concentrated. The residue was washed with diethyl ether to give the desired compound (R)-6-amino-1',8-dimethyl-2H-spiro[imidazo[1,5-a]pyridine-3,3'-piperidine]-1,5-dione (6A) as a light brown solid. Yield: 1.7 g, 98%; MS (ESI) m/z 263.3[M+1]$^+$ Synthesis of (R)-4-amino-6-((1',8-dimethyl-1,5-dioxo-1,5-dihydro-2H-spiro[imidazo[1,5-a]pyridine-3,3'-piperidin]-6-yl)amino)pyrimidine-5-carbonitrile (Cpd. No. 2Fa)

To a solution of (R)-6-amino-1',8-dimethyl-2H-spiro[imidazo[1,5-a]pyridine-3,3'-piperidine]-1,5-dione (6A, 1.70 g, 6.4 mmol) in tert-butanol (25 mL) were added 4-amino-6-chloropyrimidine-5-carbonitrile (7, 1.0 g, 6.4 mmol) and p-toluenesulfonic acid (1.10 g, 6.4 mmol). The reaction mixture was heated at 120° C. for 15 h in a sealed tube. Then the reaction mixture was concentrated and the residue was dissolved in 20% isopropanol/chloroform (100 mL). The organic layer was washed with a solution of saturated sodium bicarbonate solution, dried over sodium sulphate, filtered and concentrated. The residue was purified with silica gel column chromatography using combiflash (5-7% methanol in dichloromethane) to afford (R)-4-amino-6-((1',8-dimethyl-1,5-dioxo-1,5-dihydro-2H-spiro[imidazo[1,5-a]pyridine-3,3'-piperidin]-6-yl)amino)pyrimidine-5-carbonitrile (Cpd. No. 2Fa) as a white solid. Yield: 0.61 g, 25%. MS (ESI) m/z 381.13[M+1]$^+$; ee=97.94%; Rt=19.96 min, Chiralpak IC (4.6×250 mm, 5µm) using an isocratic gradient of methanol/carbon dioxide (40:60). $^1$H NMR (400 MHz, DMSO-d$_6$) δ 10.02 (s, 1H), 8.58 (s, 1H), 8.49 (s, 1H), 8.34 (s, 1H), 7.79 (bs, 2H), 3.31-3.28 (m, 1H), 2.98-2.94 (m, 1H), 2.82-2.81 (m, 1H), 2.45 (s, 3H), 2.23 (s, 3H), 1.99-1.94 (m, 2H), 1.72-1.70 (m, 1H), 1.50 (d, J=12.76 Hz, 1H).

Synthesis of (S)-6-amino-1',8-dimethyl-2H-spiro[imidazo[1,5-a]pyridine-3,3'-piperidine]-1,5-dione (6B)

To a solution of tert-butyl (S)-(1',8-dimethyl-1,5-dioxo-1,5-dihydro-2H-spiro[imidazo[1,5-a]pyridine-3,3'-piperidin]-6-yl)carbamate (5B, 3.40 g, 9.3 mmol) in dichloromethane (30 mL) was added 4 M hydrogen chloride in 1,4-dioxane (30 mL). The reaction mixture was stirred at room temperature for 3 h. After completion, the reaction mass was concentrated under vacuum and crude compound was suspended in saturated solution of sodium bicarbonate. The aqueous layer was extracted with dichloromethane; the organic layer was dried over sodium sulphate and concentrated. The residue was washed with diethyl ether to give the desired compound (S)-6-amino-1',8-dimethyl-2H-spiro[imidazo[1,5-a]pyridine-3,3'-piperidine]-1,5-dione (6B) as a light brown solid. Yield: 2.1 g, 85%; MS (ESI) m/z 263.3 [M+1]$^+$.

Synthesis of (S)-4-amino-6-((1',8-dimethyl-1,5-dioxo-1,5-dihydro-2H-spiro[imidazo[1,5-a]pyridine-3,3'-piperidin]-6-yl)amino)pyrimidine-5-carbonitrile (Cpd. No. 2Fb)

To a solution of (S)-6-amino-1',8-dimethyl-2H-spiro[imidazo[1,5-a]pyridine-3,3'-piperidine]-1,5-dione (6B, 2.0 g, 7.6 mmol) in tert-butanol (30 mL) were added 4-amino-6-chloropyrimidine-5-carbonitrile (7, 1.17 g, 7.6 mmol) and p-toluenesulfonic acid (1.30 g, 7.6 mmol). The reaction mixture was heated at 120° C. for 15 h in a sealed tube. Then the reaction mixture was concentrated and the residue was dissolved in 20% isopropanol/chloroform (100 mL). The organic layer was washed with a solution of saturated sodium bicarbonate solution, dried over sodium sulphate, filtered and concentrated. The residue was purified with silica gel column chromatography using combiflash (5-7% methanol in dichloromethane) to afford (S)-4-amino-6-((1',8-dimethyl-1,5-dioxo-1,5-dihydro-2H-spiro[imidazo[1,5-a]pyridine-3,3'-piperidin]-6-yl)amino)pyrimidine-5-carbonitrile (Cpd. No. 2Fb) as a white solid. Yield: 0.49 g, 18%. MS (ESI) m/z 381.17[M+1]$^+$; ee=95.58%, Rt=8.89 min, Chiralpak IC (4.6×250 mm, 5µm) using an isocratic gradient of methanol/carbon dioxide (40:60). $^1$H NMR (400 MHz, DMSO-d$_6$) δ 10.02 (s, 1H), 8.58 (s, 1H), 8.49 (s, 1H), 8.34 (s, 1H), 7.79 (bs, 2H), 3.29-3.28 (m, 1H), 2.94-2.91 (m, 1H), 2.81-2.80 (m, 1H), 2.45 (s, 3H), 2.22 (s, 3H), 1.93-1.88 (m, 2H), 1.72-1.70 (m, 1H), 1.49 (d, J=12.76 Hz, 1H).

Example 3

Utilizing appropriate reactants the following compounds can be made according to general methods 1 or 2.

| Compound No. | Structure |
|---|---|
| 3A | (structure) |
| 3B | (structure) |

| Compound No. | Structure |
|---|---|
| 3C | (structure) |
| 3D | (structure) |
| rac-1F | (structure) |
| 3E | (structure) |
| 3F | (structure) |––

| Compound No. | Structure |
|---|---|
| 3G | (structure) |
| 3H | (structure) |
| 3I | (structure) |
| 3J | (structure) |
| 3K | (structure) |

| Compound No. | Structure |
|---|---|
| 3L | 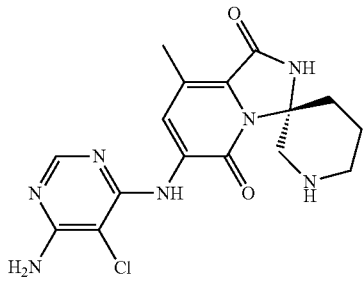 [SMILES: Cc1cc(Nc2ncnc(N)c2Cl)c(=O)n2c1C(=O)N[C@@]21CCCNC1] |
| 3M | 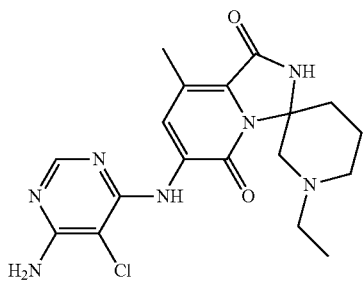 [SMILES: CCN1CCCC2(C1)NC(=O)c1c(C)cc(Nc3ncnc(N)c3Cl)c(=O)n12] |
| 3N | 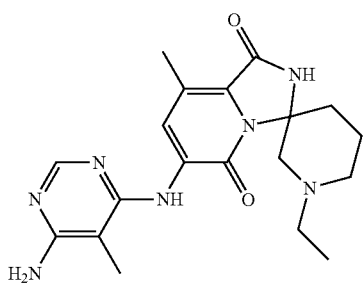 [SMILES: CCN1CCCC2(C1)NC(=O)c1c(C)cc(Nc3ncnc(N)c3C)c(=O)n12] |
| 3O | 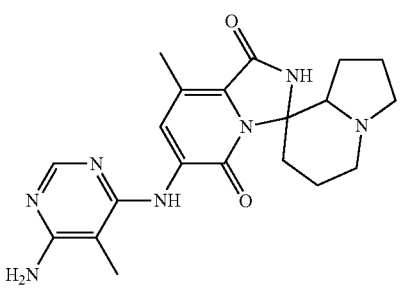 [SMILES: Cc1cc(Nc2ncnc(N)c2C)c(=O)n2c1C(=O)NC21CCCN2CCCC21] |
| 3P | 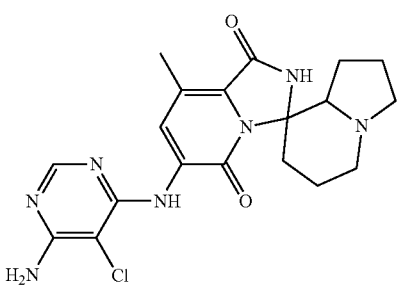 [SMILES: Cc1cc(Nc2ncnc(N)c2Cl)c(=O)n2c1C(=O)NC21CCCN2CCCC21] |
| Compound No. | Structure |
|---|---|
| 3Q | 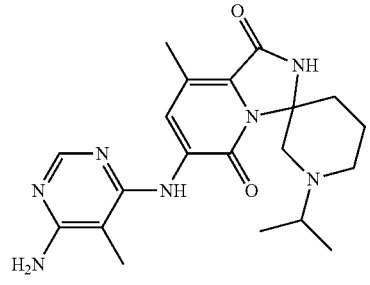 |
| 3R | 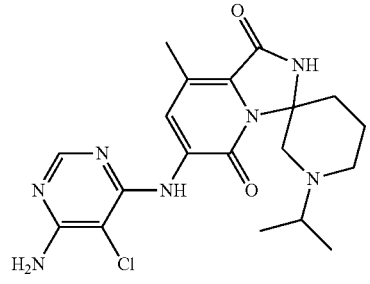 [SMILES: Cc1cc(Nc2ncnc(N)c2C)c(=O)n2c1C(=O)NC21CCCN(C(C)C)C1] |
| 3S | 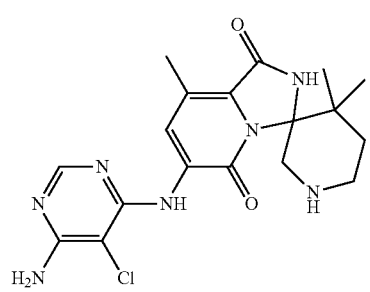 |
| 3T | 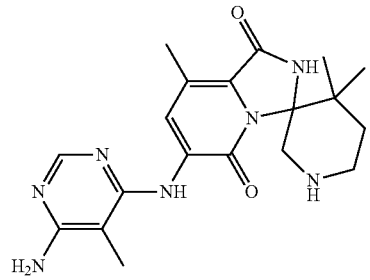 [SMILES: Cc1cc(Nc2ncnc(N)c2C)c(=O)n2c1C(=O)NC21CNCCC1(C)C] |
| 3U | 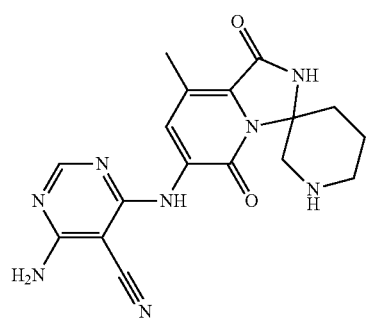 [SMILES: Cc1cc(Nc2ncnc(N)c2C#N)c(=O)n2c1C(=O)NC21CCCNC1] |

| Compound No. | Structure |
|---|---|
| rac-2F | 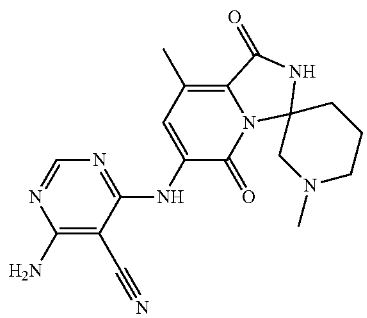 [SMILES: Cc1cc(Nc2ncnc(N)c2C#N)c(=O)n2c1C(=O)NC21CCCN(C)C1] |
| 3V | 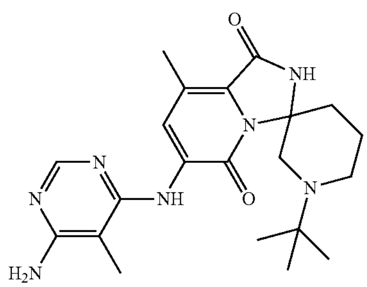 [SMILES: Cc1cc(Nc2ncnc(N)c2C)c(=O)n2c1C(=O)NC21CCCN(C(C)(C)C)C1] |
| 3W | 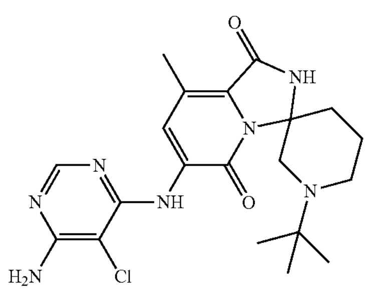 [SMILES: Cc1cc(Nc2ncnc(N)c2Cl)c(=O)n2c1C(=O)NC21CCCN(C(C)(C)C)C1] |
| 3X | 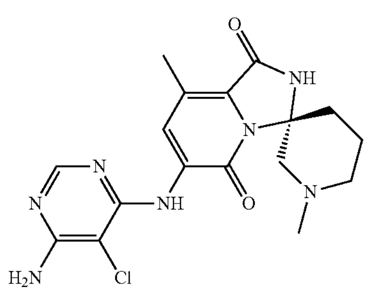 [SMILES: Cc1cc(Nc2ncnc(N)c2Cl)c(=O)n2c1C(=O)N[C@@]21CCCN(C)C1] |
| 3Y | 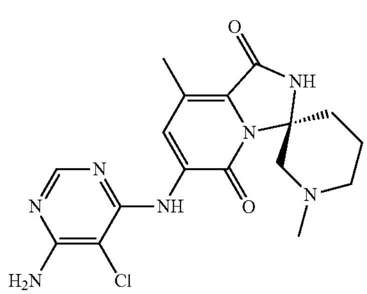 |

| Compound No. | Structure |
|---|---|
| 1Fa | 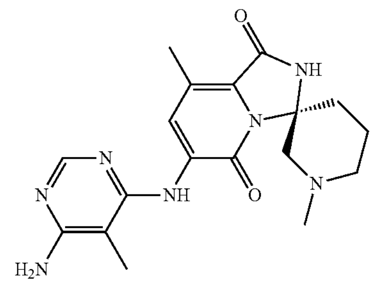 [SMILES: Cc1cc(Nc2ncnc(N)c2C)c(=O)n2c1C(=O)N[C@]21CCCN(C)C1] |
| 1Fb | 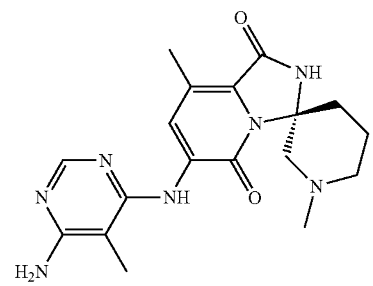 [SMILES: Cc1cc(Nc2ncnc(N)c2C)c(=O)n2c1C(=O)N[C@@]21CCCN(C)C1] |
| 2Fa | 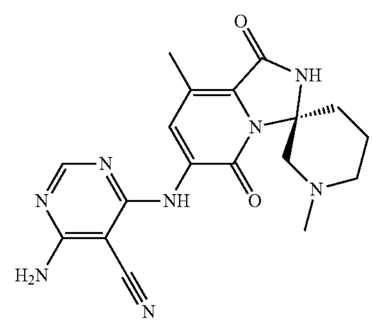 [SMILES: Cc1cc(Nc2ncnc(N)c2C#N)c(=O)n2c1C(=O)N[C@]21CCCN(C)C1] |
| 2Fb | 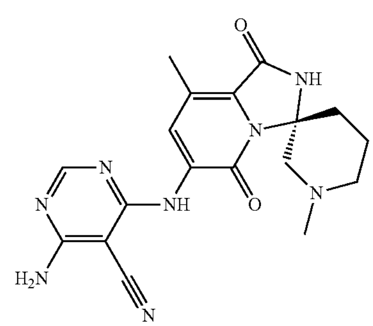 [SMILES: Cc1cc(Nc2ncnc(N)c2C#N)c(=O)n2c1C(=O)N[C@@]21CCCN(C)C1] |
| 3Z | 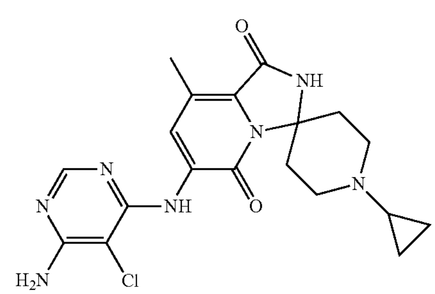 [SMILES: Cc1cc(Nc2ncnc(N)c2Cl)c(=O)n2c1C(=O)NC21CCN(C2CC2)CC1] |

| Compound No. | Structure |
|---|---|
| 3AA | 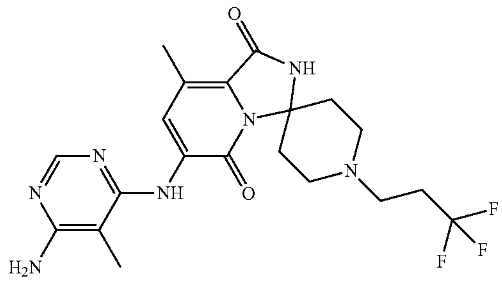 [SMILES: Cc1cc(Nc2ncnc(N)c2C)c(=O)n2c1C(=O)NC21CCN(CCC(F)(F)F)CC1] |
| 3BB | 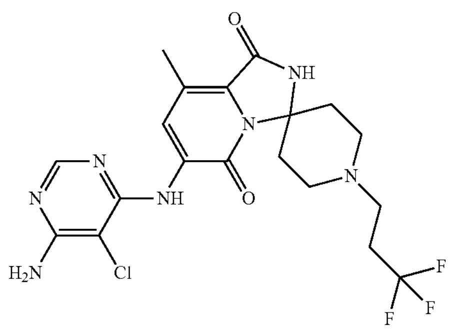 [SMILES: Cc1cc(Nc2ncnc(N)c2Cl)c(=O)n2c1C(=O)NC21CCN(CCC(F)(F)F)CC1] |
| 3CC | 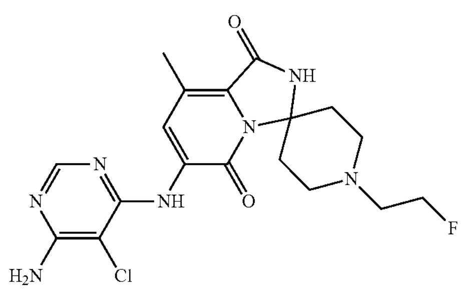 [SMILES: Cc1cc(Nc2ncnc(N)c2Cl)c(=O)n2c1C(=O)NC21CCN(CCF)CC1] |
| 3DD | 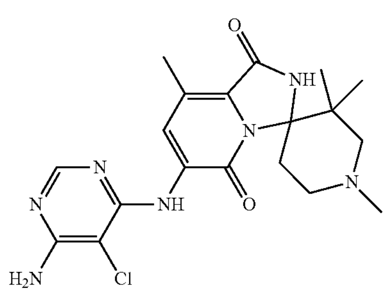 [SMILES: Cc1cc(Nc2ncnc(N)c2Cl)c(=O)n2c1C(=O)NC21CCN(C)CC1(C)C] |
| 3EE | 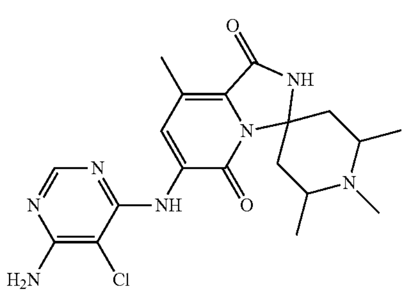 [SMILES: Cc1cc(Nc2ncnc(N)c2Cl)c(=O)n2c1C(=O)NC21CC(C)N(C)C(C)C1] |
| 3FF | |
| 3GG | |
| 3HH | |
| 3II | |
| 3JJ | |
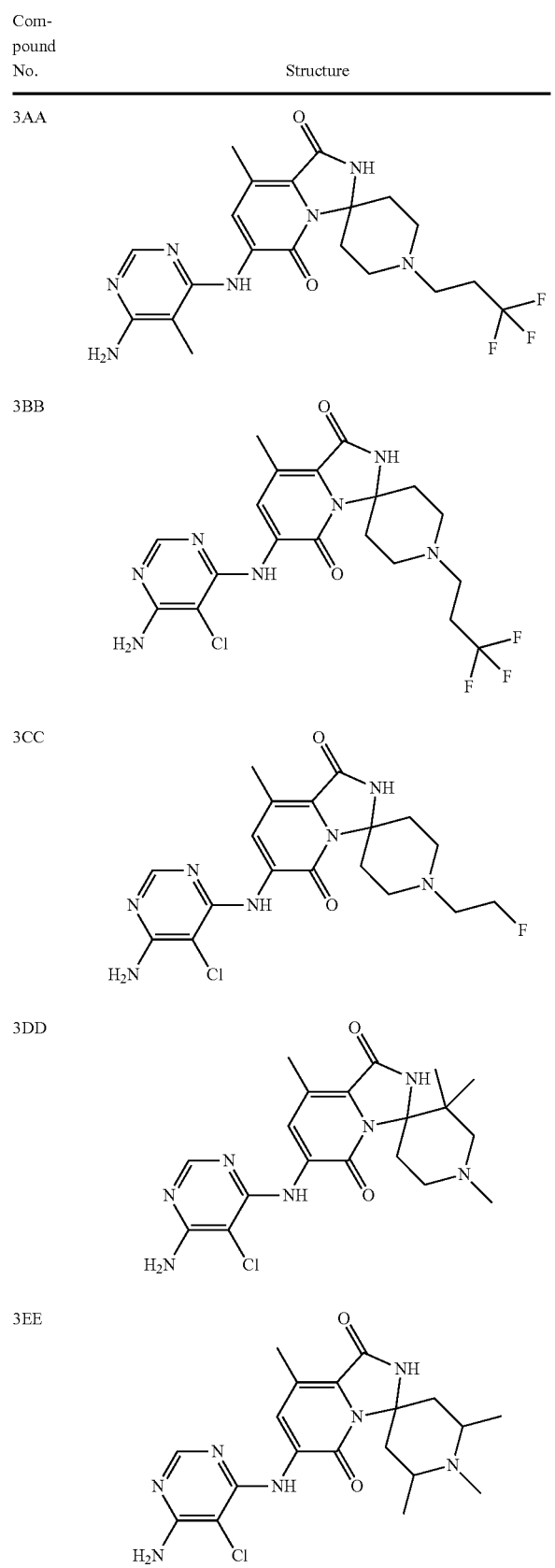
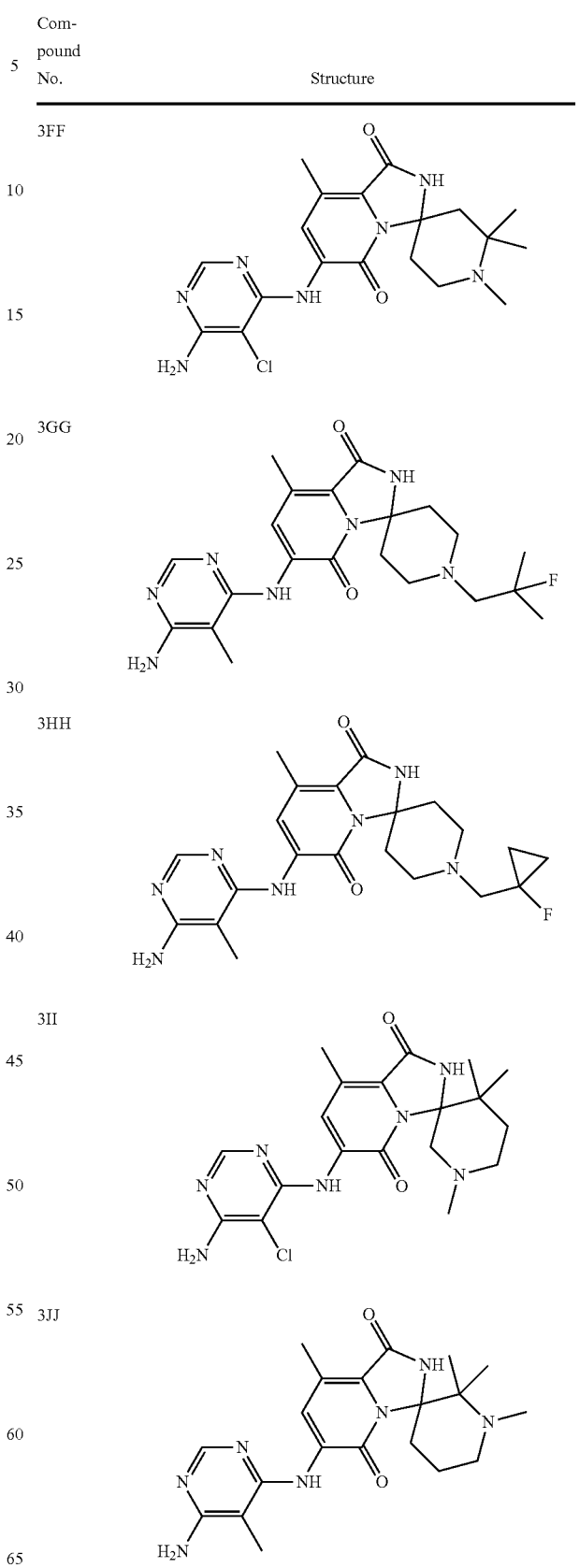

| Compound No. | Structure |
|---|---|
| 3KK | 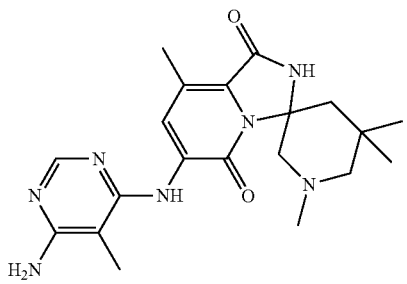 [SMILES: Cc1cc(Nc2ncnc(N)c2C)c(=O)n2c1C(=O)NC21CN(C)CC(C)(C)C1] |
| 3LL | 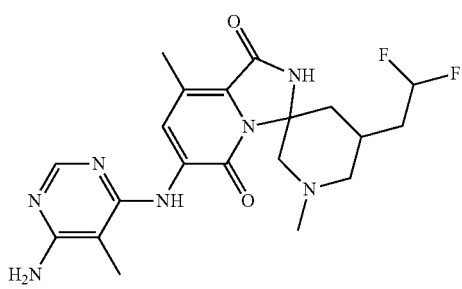 [SMILES: Cc1cc(Nc2ncnc(N)c2C)c(=O)n2c1C(=O)NC21CC(CC(F)F)CN(C)C1] |
| 3MM | 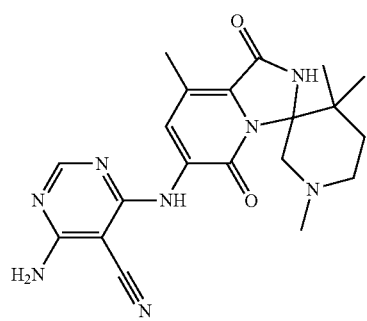 [SMILES: Cc1cc(Nc2ncnc(N)c2C#N)c(=O)n2c1C(=O)NC21CN(C)CCC1(C)C] |
| 3NN | 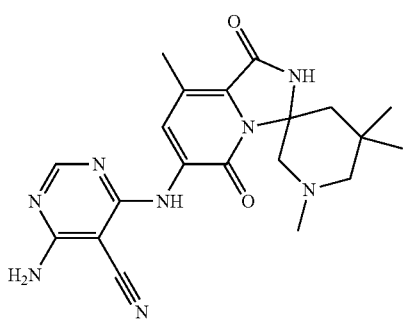 [SMILES: Cc1cc(Nc2ncnc(N)c2C#N)c(=O)n2c1C(=O)NC21CN(C)CC(C)(C)C1] |
| 3OO | 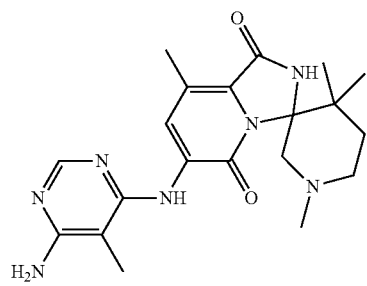 [SMILES: Cc1cc(Nc2ncnc(N)c2C)c(=O)n2c1C(=O)NC21CN(C)CCC1(C)C] |
| 3PP | 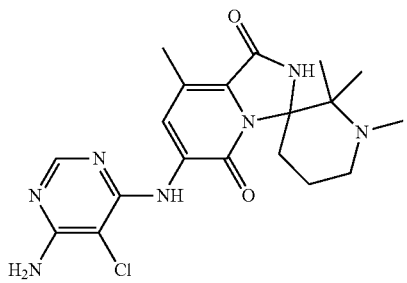 [SMILES: Cc1cc(Nc2ncnc(N)c2Cl)c(=O)n2c1C(=O)NC21CCCN(C)C1(C)C] |
| 3QQ | 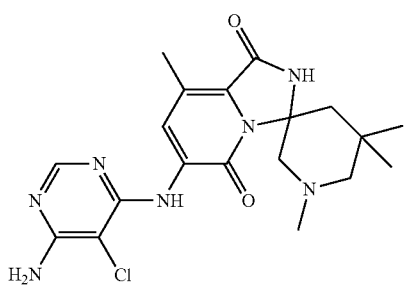 |
| 3RR | 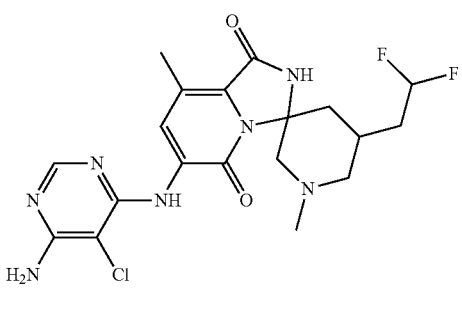 [SMILES: Cc1cc(Nc2ncnc(N)c2Cl)c(=O)n2c1C(=O)NC21CC(CC(F)F)CN(C)C1] |
| 3SS | 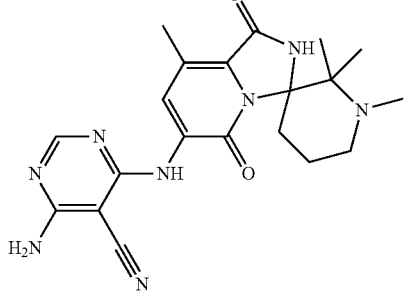 |
| 3TT | 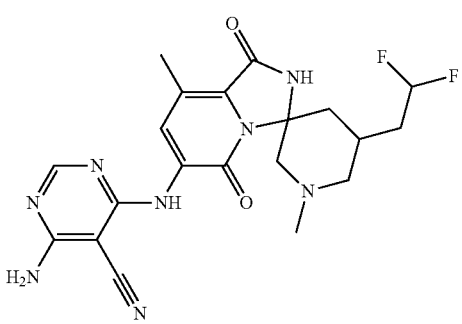 [SMILES: Cc1cc(Nc2ncnc(N)c2C#N)c(=O)n2c1C(=O)NC21CC(CC(F)F)CN(C)C1] |

Example 4: 6'-((6-amino-5-chloropyrimidin-4-yl) amino)-8'-methyl-2'H-spiro[cyclohexane-1,3'-imidazo[1,5-a]pyridine]-1',5'-dione Hydrochloride (Cpd. No. 4A)

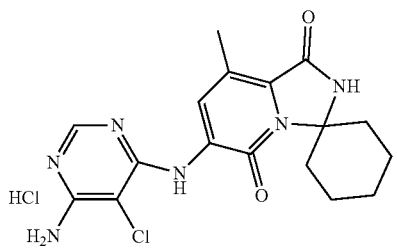

Compound 4a can be prepared according to the procedure described in Example 223 of U.S. Pat. No. 9,382,248.

Biological Studies peIF4E Signaling Cellular Assay

Phosphorylated eIF4E is assayed using the CisBio peIF4E HTRF® assay kit (CisBio, catalogue No. 64EF4PEG). Cells are plated in 96-well tissue-culture treated plate in appropriate growth medium (90 μL). Compounds (10×) are diluted using 3-fold serial dilutions in cell culture medium and added to cells. Plates are incubated for 2 hrs at 37° C. The cell supernatant is carefully removed either by aspirating supernatant or by flicking the plate. Immediately 50 μL of supplemented lysis buffer (1×) is added and incubated for at least 30 minutes at room temperature under shaking. After homogenization by pipeting up and down, 16 μL of cell lysate is transferred from the 96-well cell-culture plate to a 384-well small volume white plate. 4 μL of premixed antibody solutions (vol/vol) is prepared in the detection buffer and added. The plate is covered with a plate sealer and incubated overnight at room temperature. The fluorescence emissions at two different wavelengths are read (665 nm and 620 nm) on a Wallac Victor2. Emission ratios are converted into percent inhibitions and imported into GraphPad Prism software. The concentration of compound necessary to achieve inhibition of enzyme activity by 50% ($IC_{50}$) is calculated using concentrations ranging from 20 μM to 0.1 nM (12-point curve). $IC_{50}$ values are determined using a nonlinear regression model available in GraphPad Prism 5.

The results of these assays are set forth in Table 1 below. To this end, $IC_{50}$ values of less than 0.001 μM are labelled as "+++", from 0.001 to 0.01 μM are labelled as "++", and greater than 0.01 μM are labelled as "+" (NA means "not available").

MNK Inhibition Decreases Expression of Immune Checkpoint Receptors and Ligands

Upon activation of T cell receptor (TCR) signaling, T cells proliferate, produce cytokines (e.g., IL-2) and induce the expression of immune checkpoint receptors. Programmed death 1 (PD-1) is an inhibitory checkpoint receptor expressed on the surface of activated T cells, as well as on myeloid cells. The ligand for PD-1, programmed death ligand-1 (PD-L1, B7-H1/CD274) is not expressed by T cells or normal epithelial cells, but is expressed by antigen presenting cells and overexpressed in several cancers. Interaction of PD-1 with PD-L1 results in an anti-proliferative effect on T cells and ultimately T cell exhaustion and apoptosis. To study the role of MNK in activated T cells and tumor cells, the effect of a MNK inhibitor on molecules of immune checkpoint control was examined.

PD-1 (CD279) Expression

To examine the effect of MNK inhibitors on PD-1 expression, Jurkat cells (Clone E6.1, ATCC, transformed T cells) were used, which express PD-1 when activated through T cell receptor (TCR) signaling. Briefly, Jurkat cells were grown in 1×RPMI with 1×Pen/Strep, and 10% FBS, then about $3\times10^6$ Jurkat cells were activated in presence of 1 μg/mL PHA (Sigma) and 50 ng/mL PMA (Sigma). Test Cells were treated simultaneously with various concentrations of an MNK inhibitor (0, 0.01, 0.1, 1, 3 and 10 μM). After 48 hours, culture supernatants were harvested and examined via sandwich ELISA for the presence of IL-2 using human IL-2 ELISA DuoSet (R&D Systems, Minneapolis, Minn.). The level of PD-1 on Jurkat cells was examined by incubating with human FcR block, then contacted with allophycocyanin (APC) conjugated anti-PD-1 antibody (5 μl per 100 μl volume of test, Biolegend, San Diego, CA) for 25 minutes at 4° C., without washing the cells, fixable dead cell stain (1:10,000; BD Biosciences, San Jose, CA) was added and incubated further for 10 minutes at 4° C. Cells were washed two times with flow buffer, and finally cells were fixed with fixation buffer for 15 minutes at 4° C. After fixation, cells were washed twice with flow buffer and re-suspended in flow buffer and assessed for fluorescence using BD Accuri C6 flow cytometer. Data were analyzed using the C6 cytometer software (BD Biosciences, San Jose, CA) or Attune Nxt Cytometer (Invitrogen, Carlsbad, CA).

Activation of Jurkat T cells with PHA and PMA induced the expression of PD-1 on the cell surface of about 25-30% of the stimulated Jurkat cells as compared to uninduced cells (Unstim) and induced a 1,000-fold increase in IL-2 cytokine production, respectively. Treatment of PHA/PMA activated Jurkat T cells with the MNK inhibitor resulted in a concentration dependent decrease in the expression of the immune inhibitory receptor PD-1, up to a 50% reduction at the highest concentration as compared to control. In addition, this reduction of PD-1 was not due to a block in Jurkat T cell activation per se since MNK inhibition by an MNK inhibitor did not alter cytokine production as measured by IL-2 levels. Lastly, MNK inhibition by various different MNK inhibitors had no effect on cell viability. In fact, various different MNK inhibitors in the Jurkat T cell assay showed the ability to downregulate immune checkpoint inhibitors without affecting cell viability. The results of these assays are set forth in Table 1 below. To this end, percentage of inhibition of PD-1 positive cells (10 μM) of more than 50% are labelled as "+++", from 10% to 50% are labelled as "++", and less than 10% are labelled as "+" (NA means "not available").

Aqueous Solubility

Solubility, the phenomenon of dissolution of solute in solvent to give a homogenous system, is one of the important parameters to achieve a desired concentration of a compound in systemic circulation for desired (anticipated) pharmacological response. Compounds having good aqueous solubility are desirable because they result in good in vivo bioavailability owing to their high dissolution rate following administration to a subject. Compounds having good aqueous solubility also contribute to the ease of formulation development, formulation manufacture and stability of the formulation.

High Throughput Thermodynamic Solubility Procedure

In a 96-well plate, 10 mM DMSO stocks (50-100 uL) of each compound were dried under heated nitrogen flow using a SPE-96 plate dryer (upper flow rate=50 L/min, temperature=60° C., lower flow rate=20 L/min, temperature=80° C.). After DMSO had been completely removed, remaining materials were dissolved in test solvents including deionized water, Fasted-State Simulated Intestinal Fluid (FaSSIF, pH 6.5) and Fasted-State Simulated Gastric Fluid (FaSSGF, pH 1.6). Compounds prepared as the free base were assessed in conditions with and without one equivalent of TFA added. The theoretical maximum concentrations of the aqueous solutions were 10 mM. Each well was capped and incubated for a period of 18 hours at room temperature or 37° C. Mixing of the solutions during the incubation period was performed by either shaking the plate at 750 rpm or adding StirStix (stainless steel capillaries) and agitating the mixture using a rotary magnetic tumble stirrer. After the incubation period, aliquots from each well were filtered. Solubility of all samples were quantified following comparison to standards of known concentration by HPLC-UV.

The results of the aqueous solubility are set forth in Table 1 below.

TABLE 1 pEIF4E signaling activity, PD-1 inhibition activity and aqueous solubility

| Cpd. No. | pEI4IE signaling activity | PD-1 inhibition activity | DI H$_2$O | Aqueous Solubility FaSSGF (pH 1.2) | FaSSIF (pH 6.5) |
|---|---|---|---|---|---|
| 3-piperidine-substituted compounds | | | | | |
| 3A | + | NA | | | |
| 3B | + | | | | |
| 3C | ++ | +++ | 2.6 | 4.1 | 0.256 |
| 3D | ++ | | 3.3 | 4.4 | 0.11 |
| rac-1F | ++ | ++ | 4.3 | 9.8 | 0.24 |
| 3E | + | | | | |
| 3F | ++ | | 0.24 | 0.7 | <1 |
| 3G | ++ | | | | |
| 3H | + | | | | |
| 3I | +++ | | | | |
| 3J | ++ | | | | |
| 3K | + | +++ | 1.53 | 1.68 | 0.158 |
| 3L | ++ | +++ | 3.2 | 3.1 | 0.07 |
| 3M | | | | | |
| 3N | ++ | | | | |
| 3O | +++ | | | | |
| 3P | +++ | | | | |
| 3Q | ++ | | | | |
| 3R | +++ | | | >2.09 | 0.068 |
| 3S | ++ | +++ | 4.2 | 10 | 0.6 |
| 3T | + | ++ | 10 | 10 | 0.5 |
| 3U | + | | | | |
| rac-2F | ++ | ++ | | 1.84 | 0.079 |
| 3V | + | | | 1.82 | 0.107 |
| 3W | ++ | | | 1.4 | 0.593 |
| 3X | +++ | | | | |
| 3Y | +++ | | | | |
| 1Fa | + | ++ | >1.85 | 1.53 | 0.125 |
| 1Fb | ++ | ++ | >1.85 | >1.85 | 0.088 |
| 2Fa | ++ | ++ | 1.84 | 1.32 | 0.077 |
| 2Fb | + | ++ | 1.77 | 1.77 | 0.151 |
| 3II | | | | | |
| 3JJ | | | | | |
| 3KK | | | | | |
| 3LL | | | | | |
| 3MM | | | | | |
| 3NN | | | | | |
| 3OO | | | | | |
| 3PP | | | | | |
| 3QQ | | | | | |
| 3RR | | | | | |
| 3SS | | | | | |
| 3TT | | | | | |

TABLE 1-continued pEIF4E signaling activity, PD-1 inhibition activity and aqueous solubility

| Cpd. No. | pEI4IE signaling activity | PD-1 inhibition activity | DI H$_2$O | Aqueous Solubility FaSSGF (pH 1.2) | FaSSIF (pH 6.5) |
|---|---|---|---|---|---|
| Cycloalkyl-substituted compounds | | | | | |
| 4A | +++ | +++ | 0.0003 | 0.26 | 0.045 |
| 4-piperidine-substituted compounds | | | | | |
| 3Z | ++ | | | | |
| 3AA | ++ | + | 4.4 | 3.2 | 0.03 |
| 3BB | +++ | + | | | |
| 3CC | ++ | ++ | 0.77 | 1.9 | 0.04 |
| 3DD | +++ | +++ | 2.1 | 3 | 0.13 |
| 3EE | ++ | +++ | | | |
| 3FF | +++ | ++ | | | |
| 3GG | ++ | | | 3.6 | |
| 3HH | ++ | + | | 2.4 | 0.018 |

The inventors have unexpectedly found that the dissolution rate of an Mnk inhibitor compound can be remarkably improved over comparative compound 4a by: (i) substituting the imidazopyridine in the compound with 3- or 4-piperidine; and (ii) by substituting the pyrimidine in the compound with lower alkyl, halogen or cyano. Such substitutions or structural features induce chirality in the molecules.

The improvement in the aqueous solubility of the compounds of the invention is especially significant in low pH environments, such as in gastric or stomach fluid. For example, as shown in Table 1, compounds 3D, 3K, 3L, 3X, 3Y, rac-1F, 1Fa, 1Fb, rac-2F, 2Fa and 2Fb exhibited excellent solubility in fasted state simulated gastric fluid (FaSSGF), which has a pH value of 1.6.

Importantly, in addition to improved aqueous solubility, the 3- and 4-piperidine-substituted compounds have also retained their anti-cancer potency in the form of their ability to inhibit pEIF4E signaling. In some cases, the anti-cancer potency is further manifested in the ability of these 3- and 4-piperidine-substituted compounds to inhibit PD-1, as can be seen in Table 1.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for treating a Mnk dependent condition in a subject in need thereof, comprising administering to the subject a therapeutically effective amount of a compound having the structure

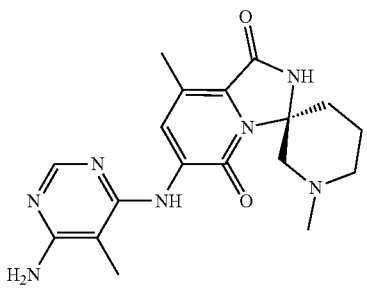

or a pharmaceutically acceptable salt thereof, wherein the Mnk dependent condition is cancer selected from the group consisting of colon cancer, breast cancer, bladder cancer, lung cancer, prostate cancer, cancer of the gastrointestinal tract, head and neck cancer, Hodgkin's lymphoma and neuroblastoma.

2. The method of claim 1, wherein the cancer is selected from non-small cell lung cancer, small cell lung cancer, urothelial cancer, head and neck cancer, and gastric cancer.

3. The method of claim 2, wherein the cancer is non-small cell lung cancer.

4. The method of claim 1, wherein the subject is a mammal.

5. A method for treating a Mnk dependent condition in a subject in need thereof, comprising administering to the subject a therapeutically effective amount of a compound having the structure

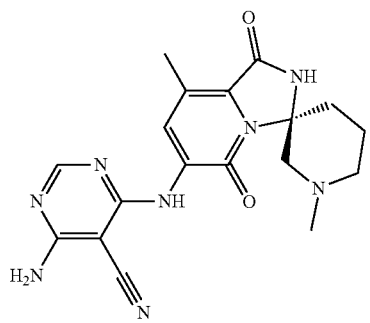

or a pharmaceutically acceptable salt thereof, wherein the Mnk dependent condition is cancer selected from the group consisting of colon cancer, breast cancer, bladder cancer, lung cancer, prostate cancer, cancer of the gastrointestinal tract, head and neck cancer, Hodgkin's lymphoma and neuroblastoma.

6. The method of claim 5, wherein the cancer is selected from non-small cell lung cancer, small cell lung cancer, urothelial cancer, head and neck cancer, and gastric cancer.

7. The method of claim 6, wherein the cancer is non-small cell lung cancer.

8. The method of claim 5, wherein the subject is a mammal.

9. A pharmaceutical composition comprising a compound selected from the group consisting of

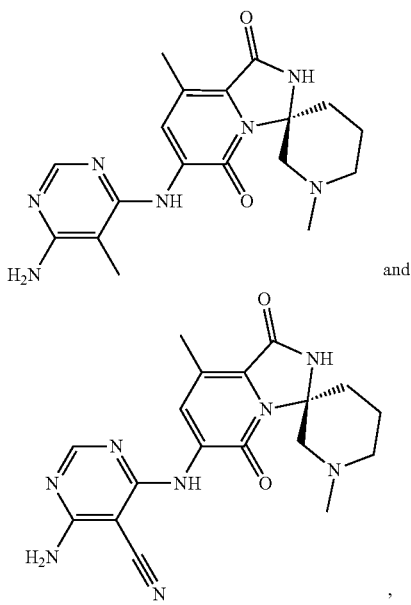

or a pharmaceutically acceptable salt thereof, and a pharmaceutically acceptable carrier.

* * * * *